(12) United States Patent  (10) Patent No.: US 8,137,352 B2
O'Neil et al.                   (45) Date of Patent:   Mar. 20, 2012

(54) EXPANDABLE INTERVERTEBRAL TOOL SYSTEM AND METHOD

(75) Inventors: Michael J. O'Neil, West Barnstable, MA (US); Ramone A. Ruberte, Ann Arbor, MI (US); Shawn D. Stad, Fall River, MA (US); John Riley Hawkins, Cumberland, RI (US)

(73) Assignee: DePuy Spine, Inc., Raynham, MA (US)

( * ) Notice: Subject to any disclaimer, the term of this patent is extended or adjusted under 35 U.S.C. 154(b) by 1031 days.

(21) Appl. No.: 11/581,668

(22) Filed: Oct. 16, 2006

(65) Prior Publication Data

US 2008/0177294 A1    Jul. 24, 2008

(51) Int. Cl.
*A61B 17/32*    (2006.01)
(52) U.S. Cl. .......................................... 606/79; 606/167
(58) Field of Classification Search ................... 606/45, 606/46, 79, 80, 81, 82, 83, 84, 85, 167–189; 623/17.11–17.16
See application file for complete search history.

(56) References Cited

U.S. PATENT DOCUMENTS

| 5,071,424 | A | * | 12/1991 | Reger | 606/159 |
| 5,108,419 | A | * | 4/1992 | Reger et al. | 606/200 |
| 5,176,693 | A | * | 1/1993 | Pannek, Jr. | 606/159 |
| 5,685,840 | A | | 11/1997 | Schechter et al. | |
| 5,792,158 | A | * | 8/1998 | Lary | 606/159 |
| 6,066,149 | A | * | 5/2000 | Samson et al. | 606/159 |
| 6,224,604 | B1 | | 5/2001 | Suddaby | |
| 6,383,188 | B2 | | 5/2002 | Kuslich et al. | |
| 6,530,913 | B1 | | 3/2003 | Giba et al. | |
| 6,537,273 | B1 | | 3/2003 | Sosiak et al. | |
| 6,579,298 | B1 | * | 6/2003 | Bruneau et al. | 606/159 |
| 6,726,690 | B2 | | 4/2004 | Eckman | |

(Continued)

FOREIGN PATENT DOCUMENTS

WO    WO 2004/049981    6/2004

OTHER PUBLICATIONS

Search Report and Written Opinion in related EPO application (i.e., 07839433.5-1526), dated Jun. 21, 2011 (9 pages).

*Primary Examiner* — Thomas C. Barrett
*Assistant Examiner* — Christopher Beccia
(74) *Attorney, Agent, or Firm* — Maginot, Moore & Beck

(57) ABSTRACT

The invention includes a system and method for loosening of tissue. In one embodiment, an intervertebral tissue removal system includes at least one abrading member for abrading tissue in an area to be cleared and at least one expandable member operable to be expanded from a first condition to a second condition, wherein the volume defined by the at least one expandable member in the second condition is greater than the volume defined by the at least one expandable member in the first condition, the at least one expandable member operably connected to the at least one abrading member such that as the at least one expandable member expands from the first condition to the second condition, the at least one abrading member is moved from a first position to a second position. The system includes an expansion media for insertion within the at least one expandable member and an expansion media conduit for delivering the expansion media to the at least one expandable member to expand the at least one expandable member from the first condition to the second condition.

49 Claims, 15 Drawing Sheets

U.S. PATENT DOCUMENTS

| | | | |
|---|---|---|---|
| 6,746,451 B2 * | 6/2004 | Middleton et al. | 606/79 |
| 6,746,462 B1 * | 6/2004 | Selmon et al. | 606/159 |
| 6,746,463 B1 * | 6/2004 | Schwartz | 606/159 |
| 6,863,672 B2 | 3/2005 | Reiley et al. | |
| 6,884,246 B1 | 4/2005 | Sonnabend et al. | |
| 6,923,813 B2 | 8/2005 | Phillips et al. | |
| 7,241,297 B2 * | 7/2007 | Shaolian et al. | 606/80 |
| 7,488,337 B2 * | 2/2009 | Saab et al. | 606/192 |
| 7,618,457 B2 * | 11/2009 | Hudgins | 623/17.12 |
| 7,621,950 B1 * | 11/2009 | Globerman et al. | 623/17.11 |
| 2001/0034526 A1 * | 10/2001 | Kuslich et al. | 606/80 |
| 2002/0026195 A1 * | 2/2002 | Layne et al. | 606/72 |
| 2002/0183716 A1 * | 12/2002 | Herweck et al. | 604/509 |
| 2003/0028197 A1 | 2/2003 | Hanson et al. | |
| 2003/0050644 A1 | 3/2003 | Boucher et al. | |
| 2003/0233096 A1 | 12/2003 | Osorio et al. | |
| 2004/0092948 A1 | 5/2004 | Stevens et al. | |
| 2004/0236424 A1 | 11/2004 | Berez et al. | |
| 2005/0038383 A1 | 2/2005 | Kelley et al. | |
| 2005/0043737 A1 * | 2/2005 | Reiley et al. | 606/79 |
| 2005/0055097 A1 * | 3/2005 | Grunberg et al. | 623/17.11 |
| 2006/0100706 A1 | 5/2006 | Shadduck et al. | |
| 2006/0106413 A1 * | 5/2006 | Bence et al. | 606/192 |
| 2006/0135882 A1 | 6/2006 | Bleich | |
| 2006/0224160 A1 * | 10/2006 | Trieu et al. | 606/83 |
| 2006/0229625 A1 * | 10/2006 | Truckai et al. | 606/79 |
| 2006/0241566 A1 | 10/2006 | Moon et al. | |
| 2007/0005140 A1 * | 1/2007 | Kim et al. | 623/17.16 |
| 2007/0162132 A1 * | 7/2007 | Messerli | 623/17.11 |

* cited by examiner

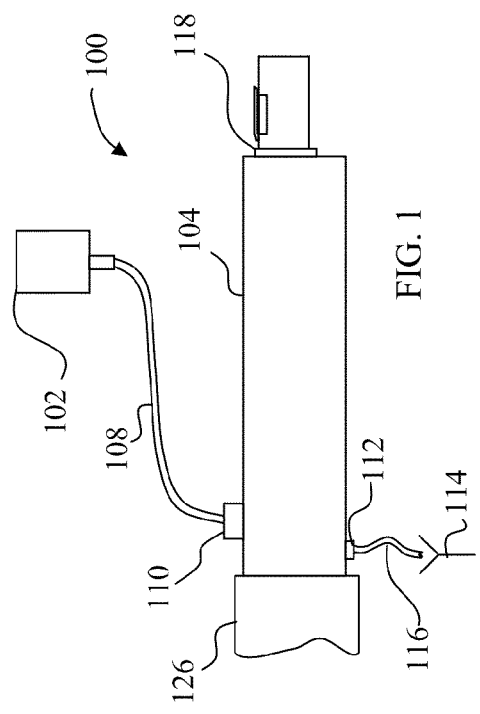
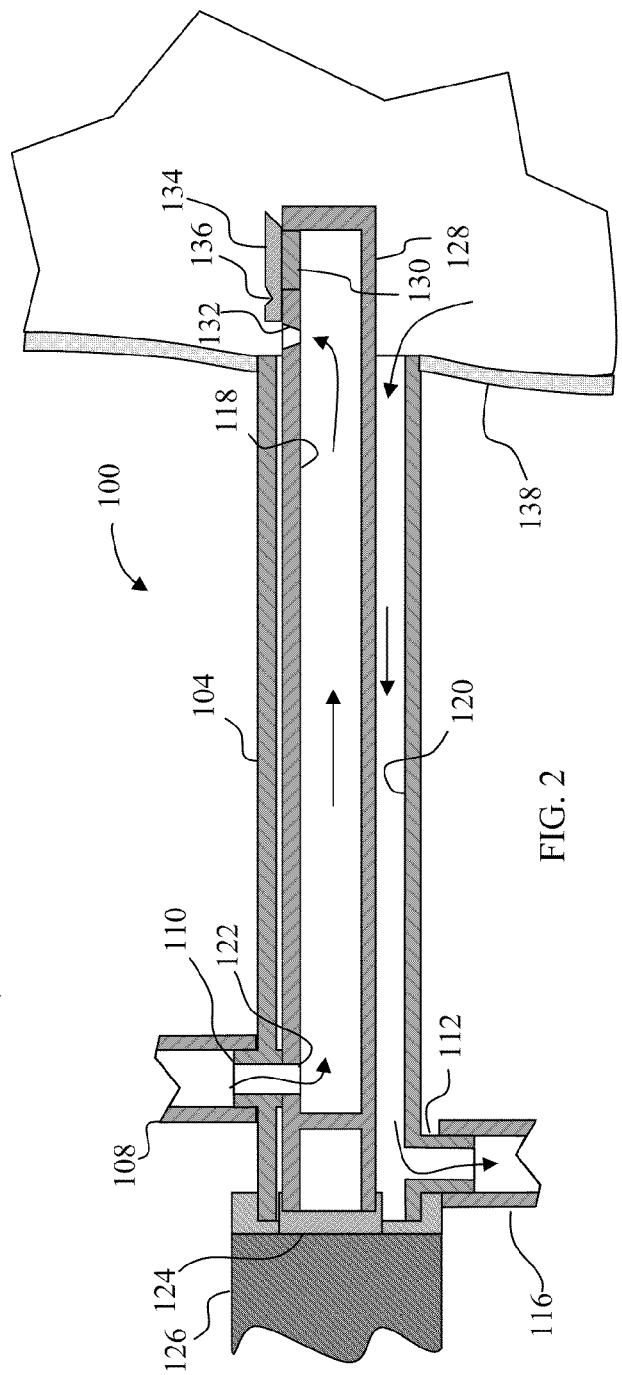

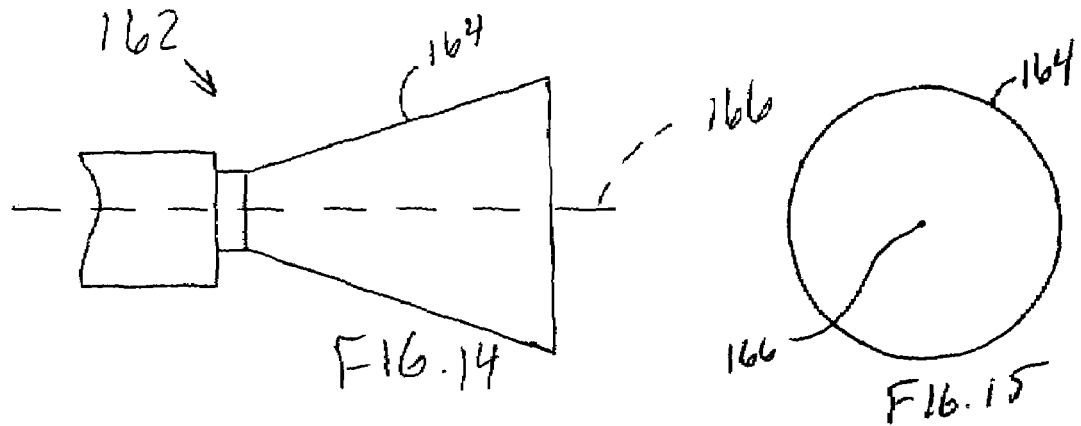
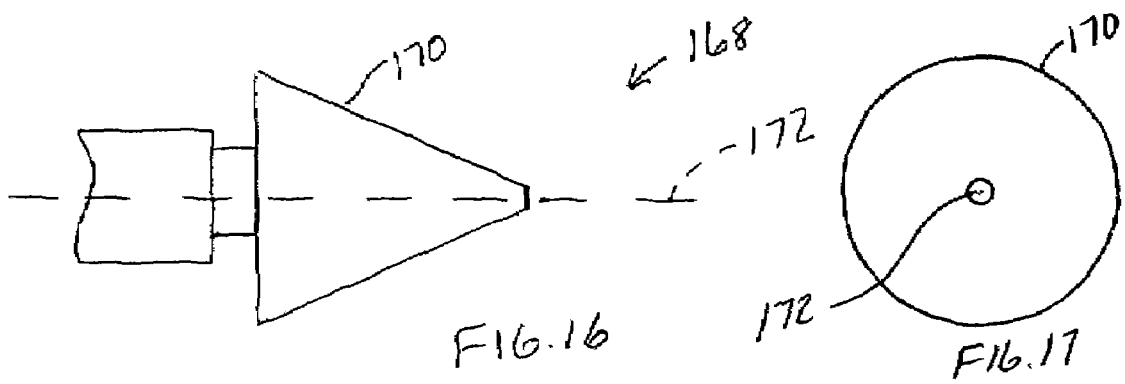
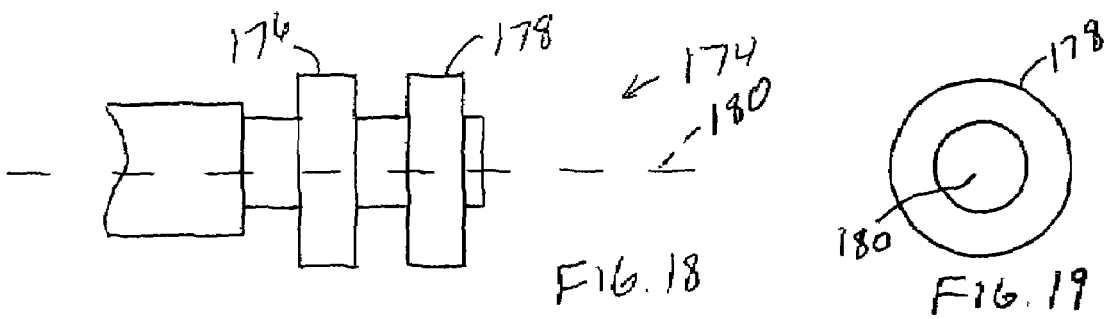
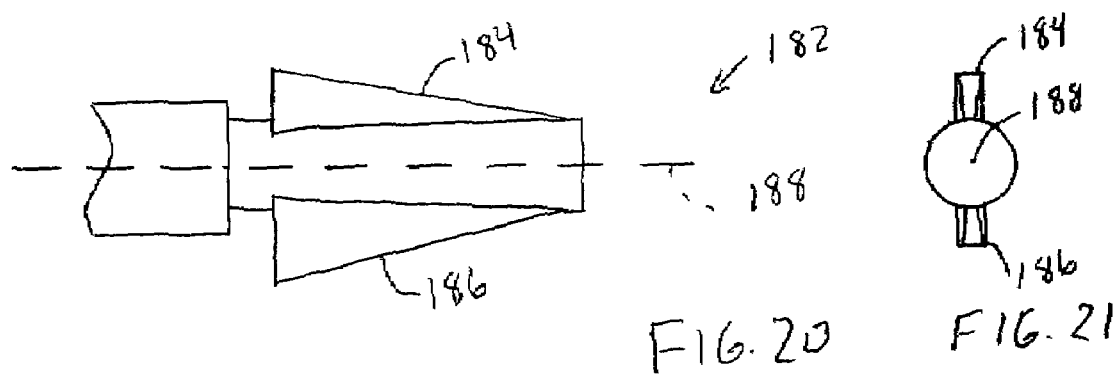

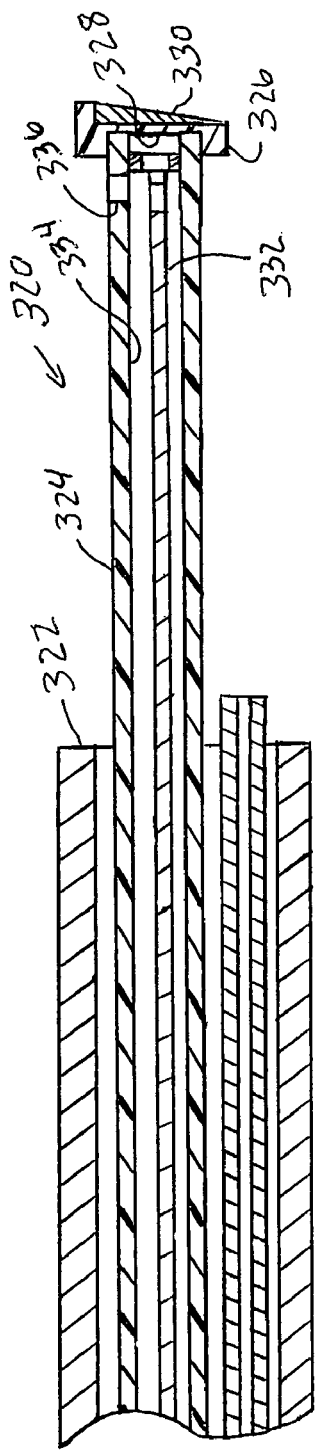
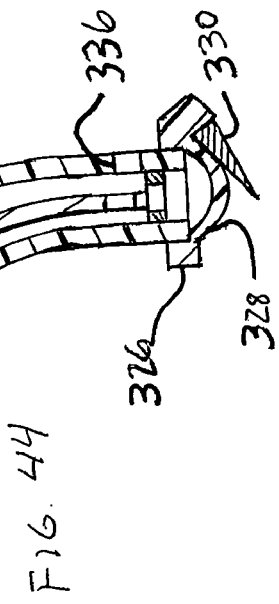
FIG. 43
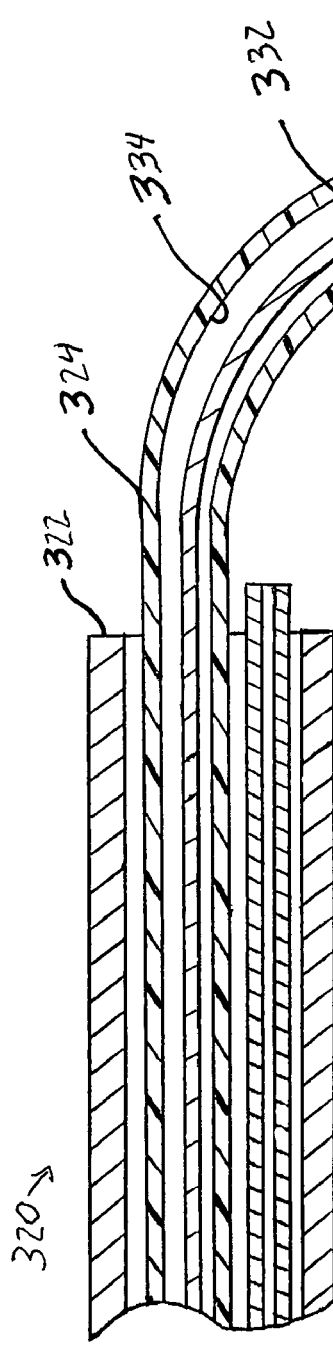
FIG. 44

EXPANDABLE INTERVERTEBRAL TOOL SYSTEM AND METHOD

FIELD OF THE INVENTION

This invention relates to surgical devices and, more particularly, to devices used to loosen tissue for removal in a surgical patient.

BACKGROUND

The spinal column acts as a major structural support. Various mechanisms, however, affect the ability of intervertebral disks to provide the requisite stability and support. For example, the normal aging process tends to weaken the bones and tissues associated with the spinal column increasing the risk of spinal injuries. Additionally, sudden movements may cause a disk to rupture or herniate. A herniation of the disk is primarily a problem when the nucleus pulposus protrudes or ruptures into the spinal canal placing pressure on nerves which in turn causes spasms, tingling, numbness, and/or pain in one or more parts of the body, depending on the nerves involved. Further deterioration of the disk can cause the damaged disk to lose height and to produce bone spurs. These mechanisms may result in a narrowing of the spinal canal and foramen, thereby causing undesired pressure on the nerves emanating from the spinal cord.

Treatments of spinal cord conditions include various procedures which involve the removal of all or a portion of a spinal component. Such procedures may include the injection of an enzyme into an affected disk to dissolve tissues. The enzymes typically used in this procedure are protein-digesting enzymes which must be carefully placed with respect to the spinal defect to avoid inadvertent dissolution of spinal tissue.

Alternatively, surgical access to a spinal area may be obtained and a tool such as a curette, osteotome, reamer, rasp, or drill may be used to mechanically reshape a component of the spinal column. The tissue removed may include disk tissue which is causing pressure on a nerve or the spinal canal. This technique is highly invasive and traumatic to the body, and therefore requires an extended recovery period. Moreover, there are increased risks of future problems due to the removal of a portion of the lamina which is no longer in place to support and protect the spinal canal at the area where the surgery took place.

Surgical access may also be used for spinal fusion surgery. In a fusion procedure, a damaged disk may be completely removed. Parts of a bone from another part of the patient's body, such as the pelvis, are harvested, and the bone parts or grafts are subsequently placed between the adjacent vertebrae so that the adjacent vertebrae grow together in a solid mass. The recovery time for a normal spinal fusion surgery is significant due not only to the fact that normal movement cannot be allowed until detectable bone growth has occurred between the bone grafts and the adjacent vertebrae, but also due to the fact that the associated ligaments and muscles, both at the spinal location and the location where the bone grafts were harvested, must also recover.

Recently, efforts have been directed to replacing defective spinal column components. When this type of procedure is performed in a minimally invasive manner, it is known for various devices implanted during the procedure to be subsequently expelled from the intervertebral disks. This expulsion is frequently attributed to inadequate clearance of the nucleus during the minimally invasive surgical procedure. The result is that the interdiskal device extrudes from the cavity formed in the spinal column, increasing the potential for expulsion.

A need exists for a device for loosening tissue that is minimally invasive, easy to use, and safe. A further need exists for a device that may be used to loosen tissue associated with an area of the spinal column. Additionally, a device which can create a relatively large cavity through a small entry point is needed. A further need exists for a device which provides for both the loosening of tissue and the removal of loosened tissue.

SUMMARY

A system and method for loosening of tissue is disclosed. In accordance with one embodiment according to the invention an intervertebral tissue removal system includes at least one abrading member for abrading tissue in an area to be cleared and at least one expandable member operable to be expanded from a first condition to a second condition, wherein the volume defined by the at least one expandable member in the second condition is greater than the volume defined by the at least one expandable member in the first condition, the at least one expandable member operably connected to the at least one abrading member such that as the at least one expandable member expands from the first condition to the second condition, the at least one abrading member is moved from a first position to a second position. The system includes an expansion media for insertion within the at least one expandable member; and an expansion media conduit for delivering the expansion media to the at least one expandable member to expand the at least one expandable member from the first condition to the second condition.

In accordance with another embodiment an intervertebral tissue removal system includes at least one abrading member for abrading tissue in an area to be cleared and at least one deformable member operable to be deformed from a first shape to a second shape, the at least one deformable member operably connected to the at least one abrading member such that as the at least one deformable member deforms from the first shape to the second shape, the at least one abrading member is moved from a first position to a second position. The system includes an expansion media for insertion within the at least one deformable member and an expansion media conduit connected to the at least one deformable member for delivering the expansion media to the at least one deformable member to deform the at least one deformable member from the first shape to the second shape.

In one embodiment, a method of loosening intervertebral tissue includes inserting at least one abrading member for abrading tissue into an area to be cleared and expanding at least one expandable member from a first condition to a second condition, wherein the volume defined by the at least one expandable member in the second condition is greater than the volume defined by the at least one expandable member in the first condition. The inserted at least one abrading member is moved from a first position to a second position by the expansion of the at least one expandable member. The method includes manipulating the inserted at least one abrading member to loosen tissue and removing the loosened tissue from the area to be cleared.

The above-described features and advantages, as well as others, will become more readily apparent to those of ordinary skill in the art by reference to the following detailed description and accompanying drawings.

BRIEF DESCRIPTION OF THE DRAWINGS

FIG. 1 shows a schematic view of an intervertebral tissue removal system with a single abrading member on a node of an expandable member wherein aspiration fluid is fed into an expansion media conduit through an inlet on a cannula to provide expansion media incorporating principles of the present invention;

FIG. 2 shows a cross-sectional view of the flow path of aspiration fluid through the cannula, conduit and expandable member of FIG. 1;

FIG. 14 shows a partial side plan view of an alternative embodiment of an expandable member in an expanded condition which includes a single node configured to provide a conical cavity that is enlarged away from the point of entry of the expandable member into a tissue space when used with an abrading member incorporating principles of the present invention;

FIG. 15 shows a front plan view of the expandable member of FIG. 14;

FIG. 16 shows a partial side plan view of an alternative embodiment of an expandable member in an expanded condition which includes a single node configured to provide a conical cavity that is enlarged near the point of entry of the expandable member into a tissue space when used with an abrading member incorporating principles of the present invention;

FIG. 17 shows a front plan view of the expandable member of FIG. 16;

FIG. 18 shows a partial side plan view of an alternative embodiment of an expandable member in an expanded condition which includes a two nodes which are symmetrical to each other and symmetrical about the longitudinal axis of the expandable member incorporating principles of the present invention;

FIG. 19 shows a front plan view of the expandable member of FIG. 18;

FIG. 20 shows a partial side plan view of an alternative embodiment of an expandable member in an expanded condition which includes a two nodes which are symmetrical to each other and symmetrical along the longitudinal axis of the expandable member incorporating principles of the present invention;

FIG. 21 shows a front plan view of the expandable member of FIG. 20;

FIG. 43 shows a plan view of an alternative expandable member with a guide rod that extends within a flexible expansion conduit in accordance with principles of the present invention; and FIG. 44 shows a plan view of the expandable member of FIG. 43 with the guide rod bent and the node in an expanded condition.

DETAILED DESCRIPTION

Figure 3:
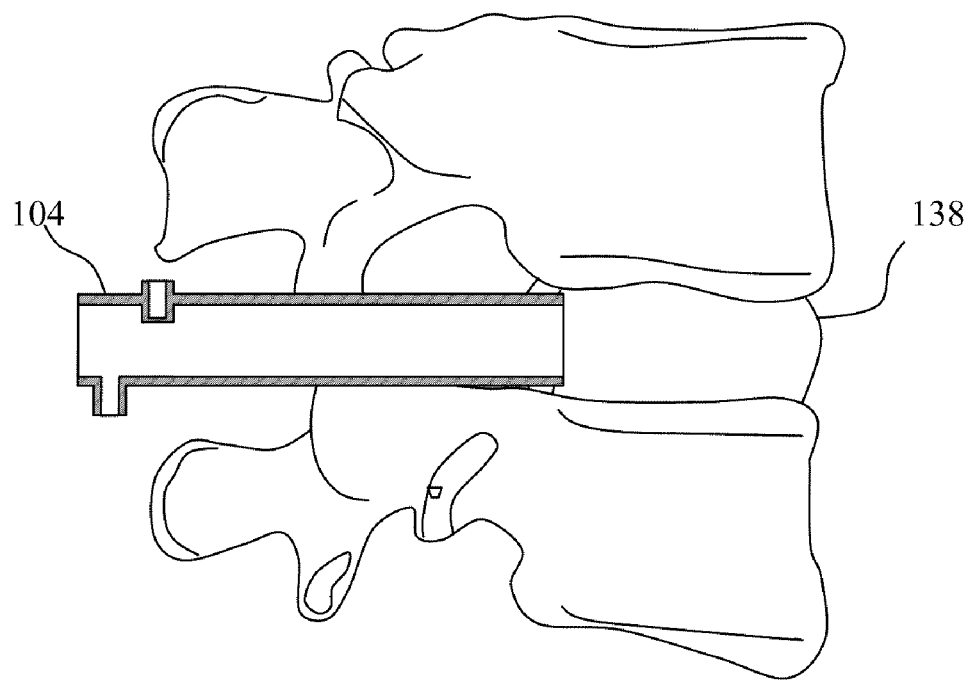
FIG. 3 shows a partial cross-sectional view of the cannula of FIG. 1 after puncturing a disc with the cannula in preparation for forming a cavity within the disc.

FIG. 1 depicts an intervertebral tissue removal system 100 which includes a fluid reservoir 102, a cannula 104 and an expandable member 106. The fluid reservoir 102 is in fluid connection with the cannula 104 through a tube 108 which is connected to a fluid inlet 110. In this embodiment, the fluid reservoir 102 is configured to provide a liquid in the form of saline solution under pressure to the fluid inlet 110. The fluid may be pressurized in a number of acceptable ways such as using a gas to pressurize the fluid reservoir 102 or a pump that takes suction from the fluid reservoir 102. In alternative embodiments, the fluid may be in the form of a gas. In the embodiment of FIG. 1, however, the fluid is preferably a liquid.

An outlet port 112 is located on the cannula 104. The outlet port 112 is in fluid connection with a drain 114 through a tube 116. In alternative embodiments, the drain 114 may be replaced with a vacuum collection system so as to provide a suction source for the cannula 104 through the outlet port 112.

The expandable member 106 is connected to a conduit 118 which extends into an internal bore 120 of the cannula 104 as best seen in FIG. 2. The expandable member 106 may be formed integrally with the conduit 118. Alternatively, the expandable member 106 may be removably coupled to the conduit 118 to allow for the use of different expandable members with the intervertebral tissue removal system 100.

Continuing with FIG. 2, the conduit 118 is in fluid connection with the fluid inlet 110 through an inlet port 122. A coupling section 124 couples the conduit 118 to a motor section 126. The motor section 126 provides motive force which is passed to the expandable member 106 through the conduit 118 and the coupling section 124. The motive force may be translational, rotational, reciprocating or oscillatory. Additionally, the motive force may be provided by motors of various types or even manually.

Regardless of the type of motion desired, the interface between the source of the motive force and the other components of the system 100, such as the conduit 118 and the cannula 104, may be designed to account for relative motion between the various components as is known to those of ordinary skill in the appropriate art. By way of example, the motor 124 in this embodiment causes the conduit 118 to reciprocate within the cannula 104. Accordingly, in addition to components such as bearings (not shown) and seals (not shown), the inlet port 122 is elongated to provide for fluid connection with the fluid inlet 110 as the conduit 118 reciprocates. Alternatively, the fluid may be provided directly to the conduit 118 without passing through the wall of the cannula 104.

The expandable member 106 includes a housing 128 with a node 130 and an orifice 132. The node 130 is sealingly attached to the housing 128 about the periphery of the node 130. The node 130 is further made of a material which is more compliant than the material used to form the housing 128. An abrading member 134 is attached to the housing 128 and extends along a portion of the node 130. A hinge 136 is provided in the abrading member 134.

Figure 4:
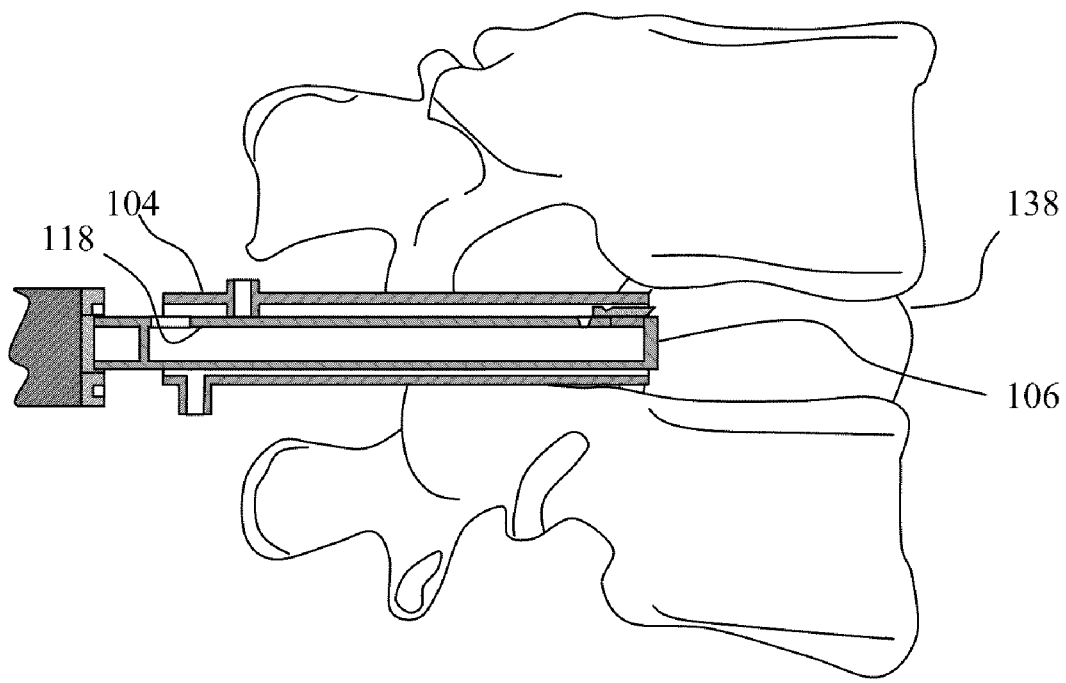
FIG. 4 shows a partial cross-sectional view of the cannula of FIG. 3 with the conduit and expandable member inserted within the cannula while the expandable member is in a deflated condition.

Operation of the intervertebral tissue removal system 100 is described with initial reference to FIG. 3. After the surgical site is prepared in an acceptable manner, the cannula 104 is used to puncture a disc 138. The conduit 118 and expandable member 106 are then inserted into the cannula 104 with the expandable member in an unexpanded condition as shown in FIG. 4. The insertion of the conduit 118 into the cannula 104 may be guided. For example, a slot and key arrangement may be used to ensure that the conduit 118 is properly aligned within the cannula 104. Once the conduit 118 has been inserted to the appropriate depth, the conduit 118 is rotated into the position shown in FIG. 2 such that the inlet port 122 is in fluid connection with the fluid inlet 110.

The desired fluid supply is then connected to the fluid inlet port 110 and the outlet port 112 is directed to a drain or a vacuum device, resulting in the configuration of FIG. 1. Specifically, the tube 108 is used to connect the fluid reservoir 102 to the fluid inlet 110 and the tube 116 is used to connect the outlet port 112 to the drain 114. Of course, the foregoing steps may be accomplished in a number of alternative variations.

For example, the fluid supply and drain tubes may be connected prior to insertion of the conduit 118 within the cannula 104. Additionally, the conduit 118 may be inserted within the cannula 104 prior to puncturing the disc 138. This may be particularly desirable when the expandable member is in a bore or drill configuration. Thus, the expandable member may be used in puncturing the disc.

Figure 5:
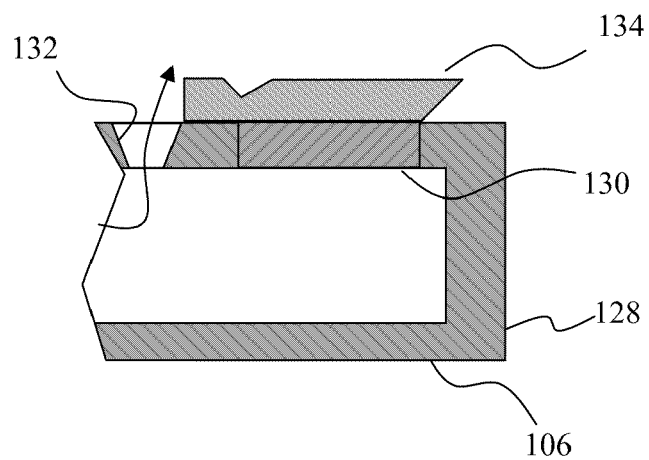
FIG. 5 shows a partial cross-sectional view of the expandable member of FIG. 1 indicating the flow path of expansion media through the expandable member when the pressure required to force the same amount of expansion media introduced into the expandable member out of the expandable member through an orifice is less than the pressure required to expand the node and the abrading member is in a first position.

Once the expandable member 106 is positioned in the desired manner within the disc 138, pressurized fluid is introduced into the conduit 118. This may be accomplished by pressurizing the fluid reservoir 102 such that pressurized fluid is directed through the tube 108 and the fluid inlet 110 into the conduit 118 by way of the inlet port 122. This flow is indicated by the single arrows in FIG. 2. As the fluid flows into the expandable member 106, the abrading member 134 is initially in the condition shown in FIG. 5.

Some of the fluid exits the expandable member 106 through the orifice 132. The orifice 132 is sized, however, to restrict the flow of fluid out of the expandable member 106. Accordingly, when pressure is initially applied to the fluid from the fluid reservoir 102, more fluid flows into the expandable member 106 than is allowed to flow out of the orifice 132. This results in increased pressure within the expandable member 106. As the pressure within the expandable member 106 increases, more fluid is forced through the orifice 132. Thus, by controlling the pressure of the fluid introduced into the conduit 118, the pressure within the expandable member 106 and thus the amount of fluid exiting the expandable member 106 through the orifice 132 may be controlled.

Moreover, because the node 130 is made from a material that is more resilient than the housing 128, the node 130 may be made to deform or flex by increasing the pressure within the expandable member 106. Accordingly, as the pressure within the expandable member 106 increases, the node 130 flexes outwardly against the abrading member 134. The hinge 136 of the abrading member 134 is constructed to bend as the pressure exerted by the node 130 on the abrading member 134 increases. Thus, the abrading member 134 is rotated from the position shown in FIG. 5 to the position shown in FIG. 6 as the volume of the expandable member increases. At this higher pressure, more water is forced through the orifice 132 as indicated by the double arrows in FIG. 6.

Figure 6:
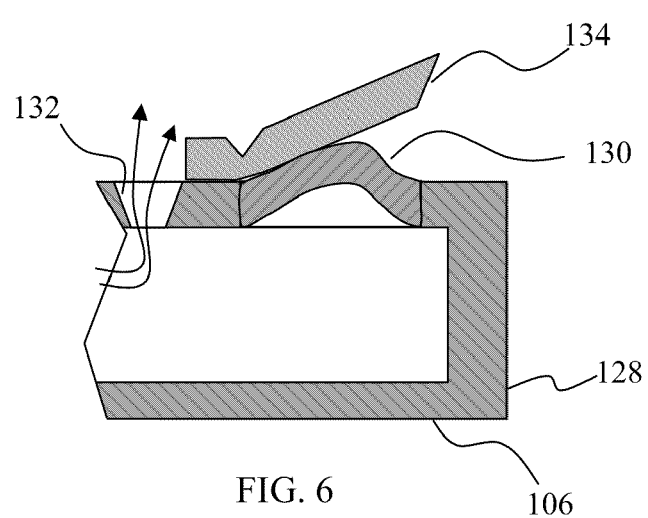
FIG. 6 shows a partial cross-sectional view of the expandable member of FIG. 1 indicating the flow path of expansion media through the expandable member when the pressure required to force the same amount of expansion media introduced into the expandable member out of the expandable member through an orifice is greater than the pressure required to expand the node such that the node flexes forcing the abrading member into a second position.

Once the abrading member 134 is in the position shown in FIG. 6, the abrading member 134 may be used to loosen tissue by moving the expandable member 106 to the right as viewed in FIG. 6. As the abrading member 134 scrapes tissue, the loosened tissue is flushed by the fluid exiting the orifice 132 toward the internal bore 120 of the cannula 104. Accordingly, the loosened tissue is directed out of the disc 138, down the internal bore 120 to the outlet port 112 as indicated by the double arrows in FIG. 2. The fluid and the excised tissue then pass through the tube 116 to the drain 114.

Thus, the expandable member 106 is used to create a cavity within the disc 138 that is larger than the diameter of the cannula 104 which is used to access the disc 138. The expandable member 106 may be used to create an even larger cavity. By way of example, further increases in the pressure of the fluid within the expandable member 106 results in additional flexing of the node 130 outwardly against the abrading member 134 as the volume of the expandable member further increases. Thus, the abrading member 134 is further rotated from the position shown in FIG. 6 to the position shown in FIG. 7. At this higher pressure, more water is forced through the orifice 132 as indicated by the triple arrows in FIG. 7.

Figure 7:
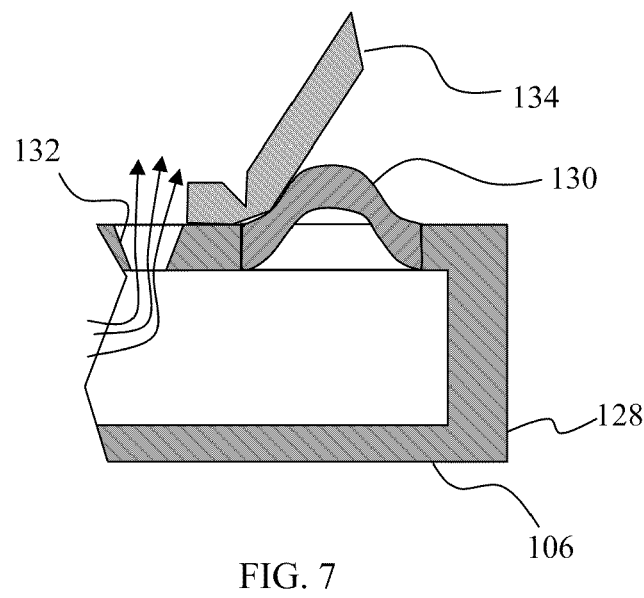
FIG. 7 shows a partial cross-sectional view of the expandable member of FIG. 1 indicating the flow path of expansion media through the expandable member when the pressure required to force the same amount of expansion media introduced into the expandable member out of the expandable member through an orifice is greater than the pressure required to expand the node to the condition shown in FIG. 6 such that the node further flexes forcing the abrading member into a third position.

Once the abrading member 134 is in the position shown in FIG. 7, the abrading member 134 may be used to loosen additional tissue by moving the expandable member 106 to the right as viewed in FIG. 7. As the abrading member 134 loosens additional tissue, the additional tissue is flushed by the fluid exiting the orifice 132 toward the internal bore 120 of the cannula 104. Accordingly, the additional tissue is directed out of the disc 138, down the internal bore 120 to the outlet port 112 as indicated by the double arrows in FIG. 2. The fluid and the additional tissue then pass through the tube 116 to the drain 114.

Accordingly, the expandable member 106 may be controlled to provide cavities having a number of different sizes merely by controlling the pressure within the expandable member 106. In one embodiment, one or more of the expandable member 106, the abrading member 134 and the conduit 118 may be constructed with a radiopaque material to enhance the detection of the position of the tissue removal system components. This allows for more precise determination of tissue clearance.

Once the desired tissue has been removed, the pressure applied to the fluid from the fluid reservoir 102 is reduced. Accordingly, less fluid flows into the expandable member 106 which results in decreased pressure within the expandable member 106. As the pressure within the expandable member 106 decreases, less fluid is forced through the orifice 132. Additionally, because the material used to construct the node 134 is resilient, as the pressure within the expandable member 106 decreases, the node 130 tends to return toward the condition depicted in FIG. 5 thereby reducing the volume of the expandable member. Additionally, the hinge 136 may be constructed of a shape retaining material. Thus, as the node 130 moves in a direction away from the abrading member 134, the hinge 136 provides rotational force to the abrading member 134 such that the abrading member is rotated, for example, from the position shown in FIG. 6 to the position shown in FIG. 7. The expandable member 106 may then be removed from the disc 138 by withdrawing the conduit 118 from the cannula 104.

Figure 8:
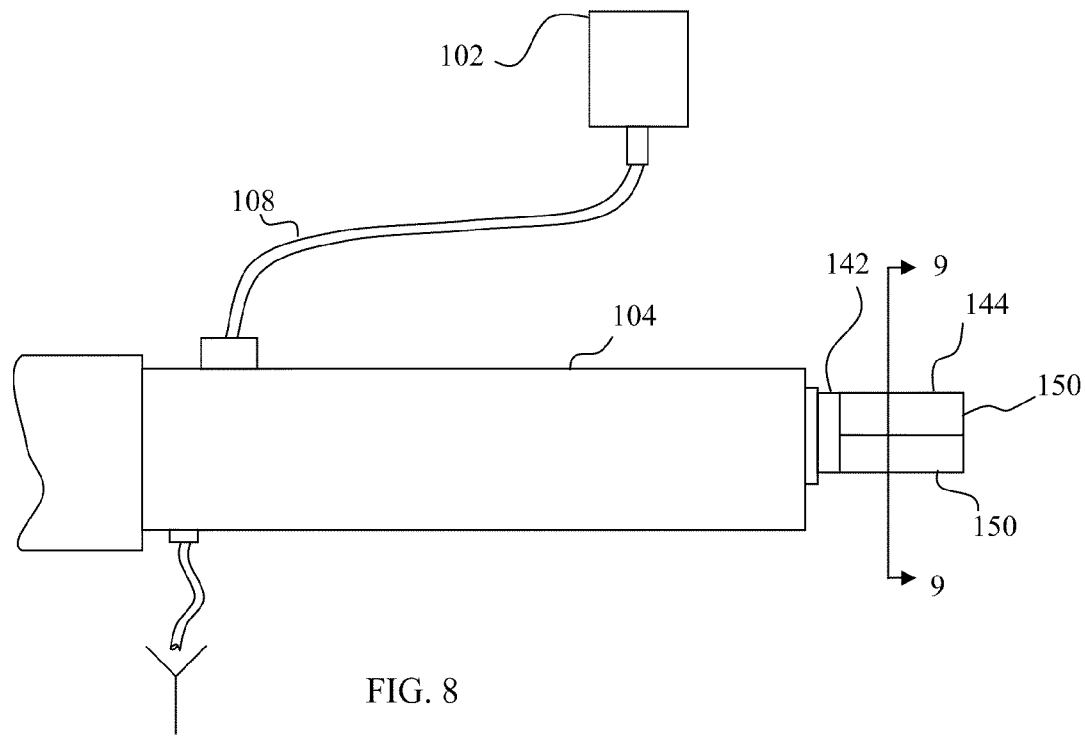
FIG. 8 shows a schematic view of an alternative intervertebral tissue removal system with a number of abrading members on a node of an expandable member wherein aspiration fluid is fed into an expansion media conduit through an inlet on a cannula to provide expansion media incorporating principles of the present invention.
Figure 9:
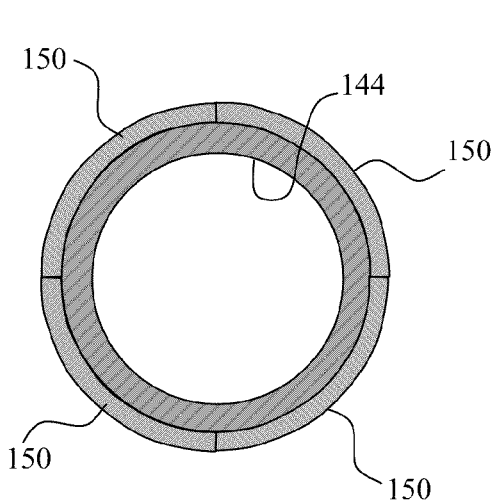
FIG. 9 shows a cross-sectional view of the expandable member and abrading members of FIG. 8 in a deflated condition.
Figure 10:
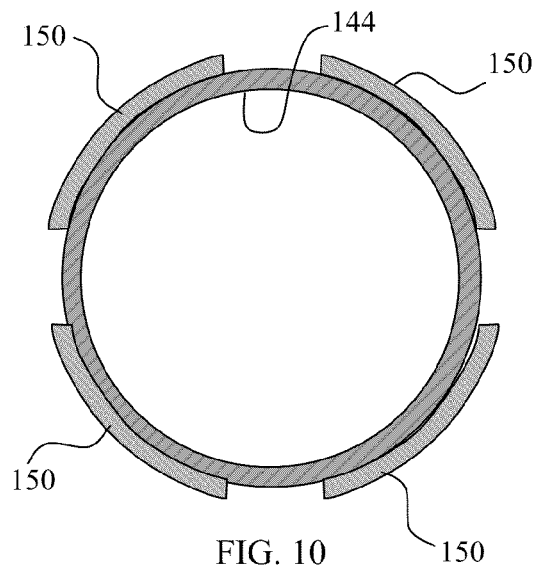
FIG. 10 shows a cross-sectional view of the expandable member and abrading members of FIG. 8 in an expanded condition wherein tissue may be loosened to form a cavity having a diameter greater than the diameter of the cannula of FIG. 8.

In an alternative embodiment shown in FIGS. 8-10, an intervertebral tissue removal system 140 includes a conduit 142 fluidly connected to an expandable member 144. A fluid reservoir 146 is connected to the conduit 142 through a tube 148 and abrasive particles 150 are adhered to the expandable member 144. The conduit 142 and the expandable member 144 are sized such that when the expandable member 144 is in the condition shown in FIGS. 8 and 9, the conduit 142 and the expandable member 144 fit within the cannula 104. In this embodiment, the conduit 142 and the expandable member 144 are not permeable to the fluid within the fluid reservoir 146. Accordingly, the fluid reservoir 146 is not used to provide aspiration fluid.

In operation, as pressurized media is introduced into the expandable member 144, the abrasive particles 150 are forced outwardly away from the longitudinal axis of the expandable member 144 to the position shown in FIG. 10. In this embodiment, the pressure inside of the expandable member 144 is maintained by the fluid reservoir 146 at a constant pressure that is greater than the pressure needed to expand the expandable member 144. The increased pressure forces the abrasive particles 150 against the tissue surrounding the expandable member 144. Accordingly, as the expandable member 144 is moved, the abrasive material 150 may be used to loosen tissue completely about the perimeter of the expandable member 144. Moreover, the increased pressure within the expandable member 144 causes the abrasive particles 150 to be constantly forced against the tissue adjacent to the expandable member 144 even as tissue is loosened. Thus, tissue is constantly being loosened so long as the expandable member 144 is being moved.

As set forth above, the fluid within the fluid reservoir 146 is not used to aspirate the cavity formed by the expandable member 144. Thus, in accordance with one method, the expandable member 144 is deflated and removed periodically to allow for an aspiration fluid to be introduced into the cavity to assist in removal of loosened tissue. This staged aspiration may be performed a number of times during a particular surgery.

Figure 11:
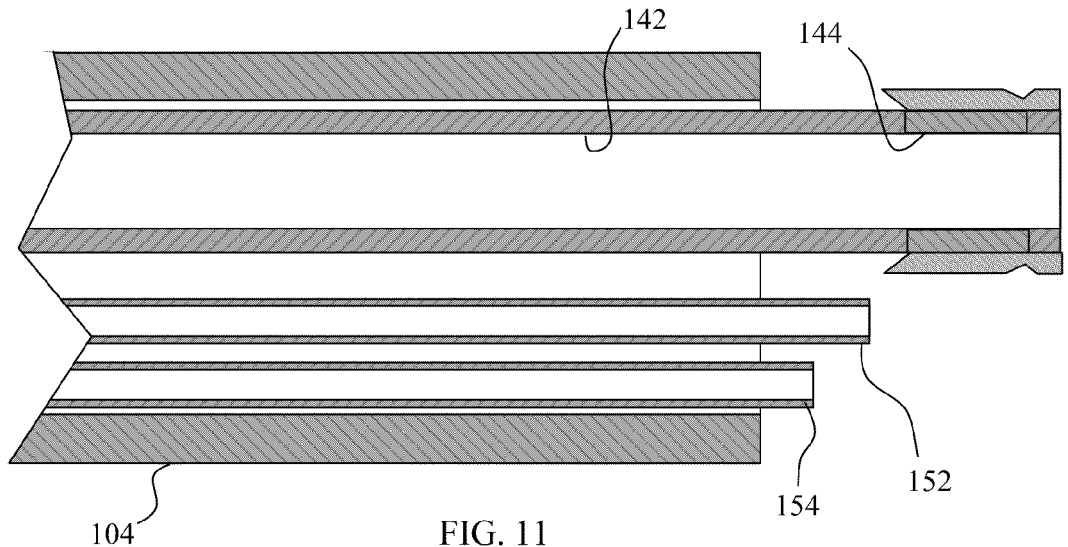
FIG. 11 shows a partial cross-sectional view of an alternative intervertebral tissue removal system wherein an aspiration fluid conduit and drainage conduit are provided to a cavity through a cannula separate from the expansion media conduit incorporating principles of the present invention.

Alternatively, as shown in FIG. 11, a dedicated aspiration tube 152 may be introduced into the cavity through the cannula 104 along with a drain tube 154 to provide for continuous aspiration of the cavity. Specifically, an aspiration fluid is provided through the aspiration tube 152 to the cavity and the aspiration fluid and any loosened tissue is removed through the drain tube 154.

Figure 12:
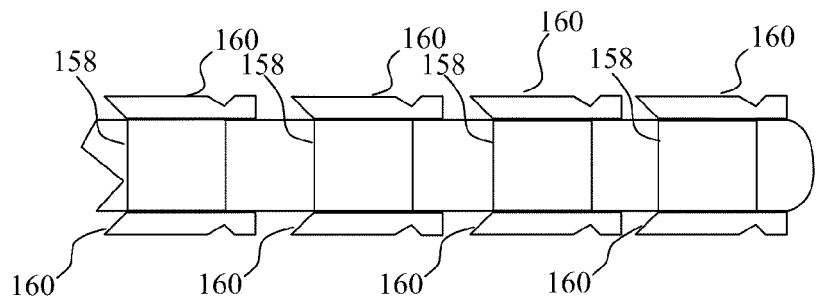
FIG. 12 shows a partial plan view of an alternative embodiment of an expandable member in an unexpanded condition which includes multiple nodes, each node operably connected to two abrading members incorporating principles of the present invention.
Figure 13:
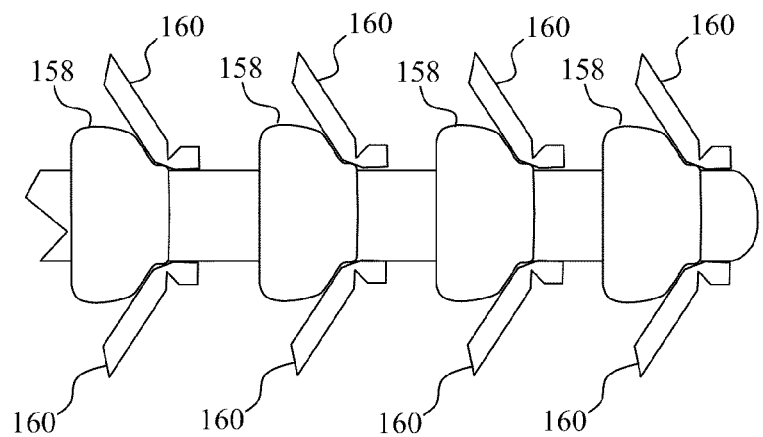
FIG. 13 shows a partial plan view of the expandable member of FIG. 12 in an expanded condition such that the abrading members are positioned to loosen tissue on two sides of the expandable member.

A number of different types of expandable members maybe used in accordance with the present invention. By way of example, FIG. 12 shows an expandable member 156. The expandable member 156 is formed and operated in a manner substantially similar to the expandable member 106. The main differences are that the expandable member 156 includes a number of nodes 158 which are in fluid connection through an inter-nodal conduit (not shown), and each of the nodes 158 is operably connected to two abrading members 160. Thus, when the nodes 158 are expanded as shown in FIG. 13, the abrading members 160 may be used to loosen tissue on opposite sides of the expandable member 156.

FIGS. 14-21 depict some alternative embodiments of expandable members in an expanded condition. The expandable member 162 shown in FIGS. 14 and 15 includes a node 164 which is symmetrical about the longitudinal axis 166 of the expandable member 162 but which is not symmetrical along the longitudinal axis 166. With reference to FIGS. 16 and 17, the expandable member 168 includes a node 170 which is symmetrical about the longitudinal axis 172 of the expandable member 168 but which is not symmetrical along the longitudinal axis 172.

The expandable member 174 shown in FIGS. 18 and 19 includes a node 176 and a node 178 which are symmetrical both to each other and about the longitudinal axis 180 of the expandable member 174. With reference to FIGS. 20 and 21, the expandable member 182 includes a node 184 and a node 186 which are symmetrical to each other but which are not symmetrical along the longitudinal axis 188 of the expandable member 182. The nodes 184 and 186 thus define flutes extending along the expandable member 182.

Figure 22:
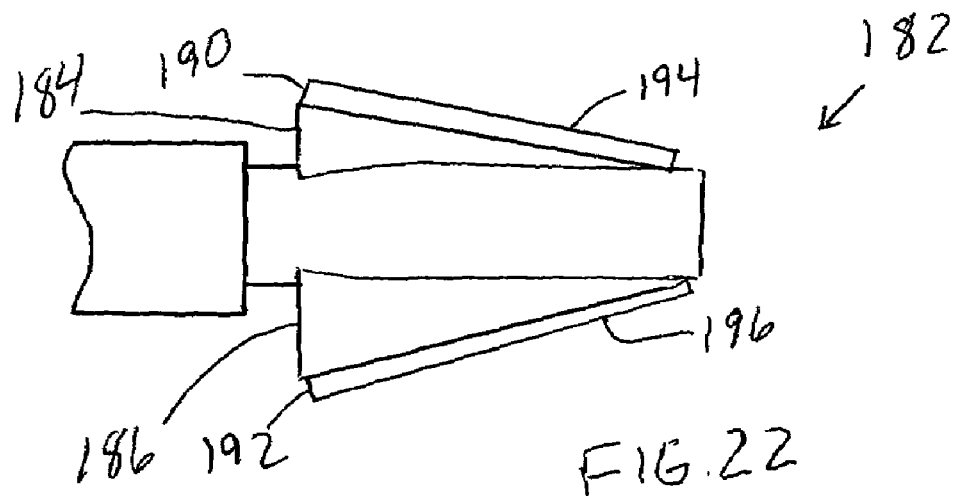
FIG. 22 shows a side plan view of the expandable member of FIG. 20 with abrading members coupled to the nodes incorporating principles of the present invention.

Various types of abrading members may be combined with the expandable members described above as well as other expandable members to provide a variety of abrading capabilities. By way of example, FIG. 22 shows the expandable member 182 of FIG. 17 with an abrading member 190 on the node 184 and an abrading member 192 on the node 186. In the embodiment of FIG. 22, the abrading members 190 and 192 are blades having cutting edges 194 and 196 that extend along a substantial portion of the length of the abrading members 190 and 192, respectively. Alternatively, the abrading members may comprise abrasive particles adhered to the nodes 184 and 186. Additionally, the abrading members 190 and 192 may be serrated, providing a number of chisel like projections along the nodes 184 and 186.

Figure 23:
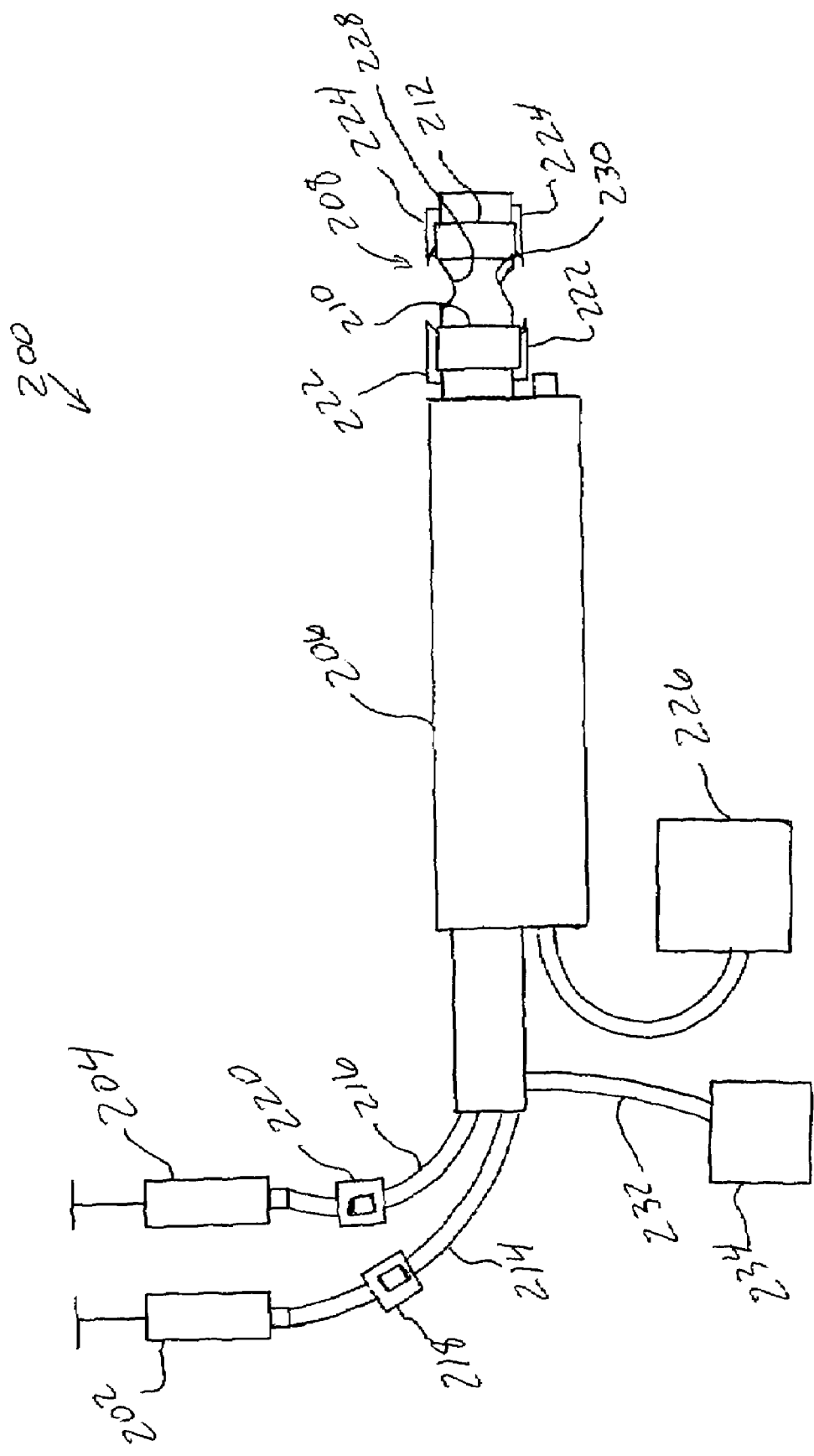
FIG. 23 shows a schematic view of an intervertebral tissue removal system with multiple abrading members on multiple nodes of an expandable member wherein expansion media is provided to each of the nodes from a first and a second syringe, respectively, and two drainage orifices are located between the nodes to provide for drainage of separately provided aspiration fluid and loosened tissue incorporating principles of the present invention.

Moreover, abrading members may be coupled to expandable members in a variety of ways to provide different abrading characteristics. By way of example, the intervertebral tissue removal system 200 shown in FIG. 23 includes two fluid reservoirs 202 and 204, a cannula 206 and an expandable member 208. The expandable member 208 includes nodes 210 and 212. The fluid reservoirs 202 and 204, which in this embodiment are syringes, are in fluid communication with the nodes 210 and 212, respectively, through tubes 214 and 216. Two valves 218 and 220 are provided along the tubes 214 and 216 which are conduits providing expansion media to the nodes 210 and 212. Each of the nodes 210 and 212 is configured to control a set of abrading members 222 and 224, respectively.

The intervertebral tissue removal system 200 further includes an aspiration fluid supply 226. An aspiration orifice 228 and an aspiration orifice 230 are in fluid connection through an aspiration conduit 232 with a collection container 234.

In operation, either of the nodes 210 and 212 may be expanded or both may be expanded, depending upon the cavity to be formed. For purposes of the present example, both nodes 210 and 212 are to be filled. Accordingly, after the expandable member 208 is positioned within a space to be abraded, the valves 218 and 220 are placed in the open position. The syringes 202 and 204 are then manipulated to force fluid from syringes 202 and 204 to the nodes 210 and 212, respectively, through the tubes 214 and 216, respectively. When the nodes 210 and 212 have been expanded such that the abrading members 222 and 224 are at the desired orientation, the valves 218 and 220 are placed in the shut position to maintain the abrading members 222 and 224 at the desired orientation.

Figure 24:
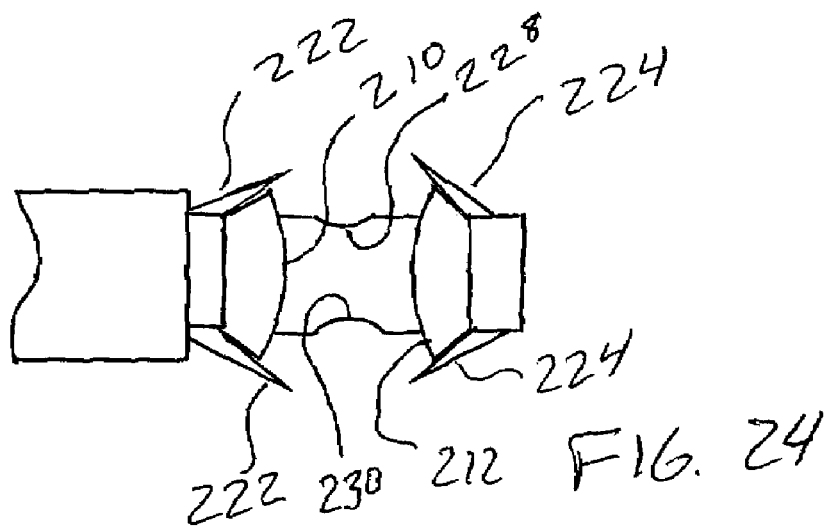
FIG. 24 shows a partial plan view of the expandable member of FIG. 23 with the nodes expanded to loosen tissue between the two sets of abrading members.

Accordingly, when the nodes 210 and 212 are expanded, the abrading members 222 and 224 face each other. Thus, as the expandable member 208 moves to the right as viewed in FIG. 24, the set of abrading members 222 will loosen tissue contacting the abrading members 222 while the set of abrading members 224 will not loosen tissue contacting the abrading members 224. As the expandable member 208 moves to the left as viewed in FIG. 24, however, the set of abrading members 224 will loosen tissue contacting the abrading members 224 while the set of abrading members 222 will not loosen tissue contacting the abrading members 222. Thus, a cavity may be formed in the area between two abrading members using the intervertebral tissue removal system 200. Advantageously, the aspiration orifices 228 and 230 are located between the abrading members 222 and 224. Thus, the movement of the abrading members 222 and 224 direct loosened tissue toward the aspiration orifices 228 and 230.

Figure 25:
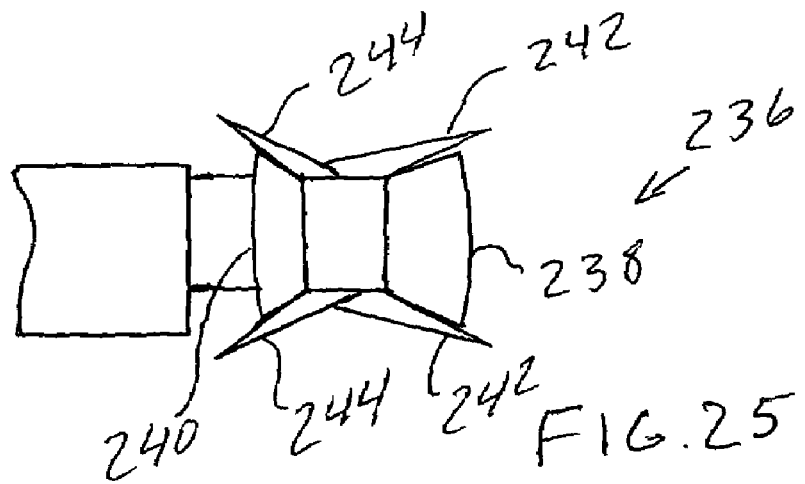
FIG. 25 shows a partial plan view of an alternative expandable member with abrading members configured on two nodes to loosen tissue outwardly of the abrading members incorporating principles of the present invention.

Alternatively, the intervertebral tissue removal system shown in FIGS. 12 and 13 may be used to form a cavity which extends in a leftward direction from the abrading member 160. In yet a further alternative embodiment, a cavity may be formed which extends in both the leftward and rightward directions. With reference to FIG. 25, the expandable member 236 includes nodes 238 and 240 which are configured to control a set of abrading members 242 and 244, respectively. When the nodes 238 and 240 are expanded as shown in FIG. 25, a cavity may be formed which extends outwardly in both the leftward and rightward directions from the abrading members 242 and 244. Therefore, the configuration of the abrading members can be selected to provide various abrading capabilities.

Figure 26:
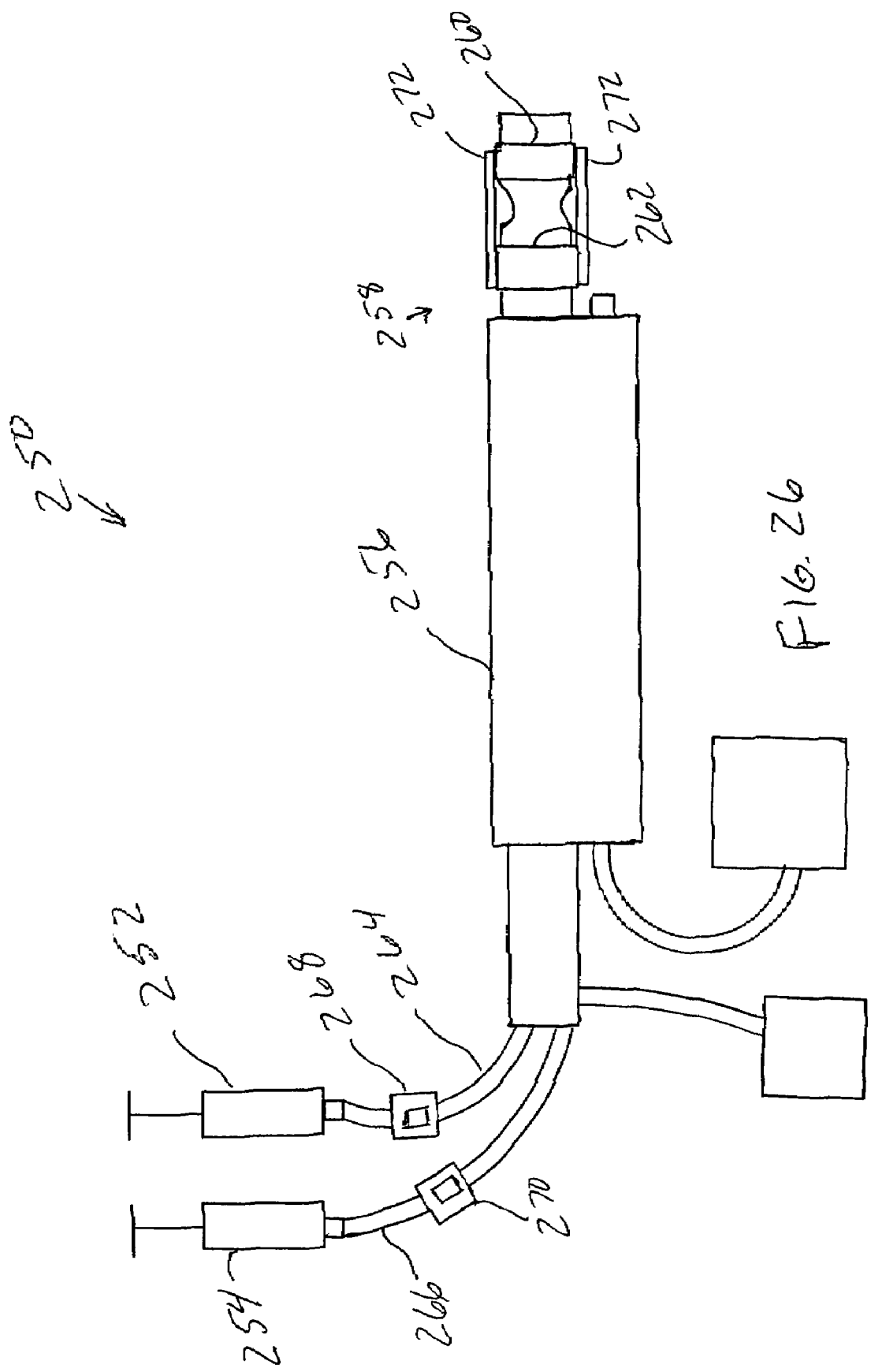
FIG. 26 shows a schematic view of an intervertebral tissue removal system that is similar to the intervertebral tissue removal system of FIG. 23, but with a different configuration of abrading members to provide cavities of different shapes incorporating principles of the present invention.

In a further embodiment shown in FIG. 26, a single intervertebral tissue removal system 250 provides the ability to form cavities of different shapes. The intervertebral tissue removal system 250 includes two fluid reservoirs 252 and 254, a cannula 256 and an expandable member 258. The expandable member 258 includes nodes 260 and 262. The fluid reservoirs 252 and 254 are in fluid communication with the nodes 260 and 262, respectively, through tubes 264 and 266. Two valves 268 and 270 are provided along the tubes 264 and 266. Abrading members 272 are attached to each of the nodes 260 and 262.

Figure 27:
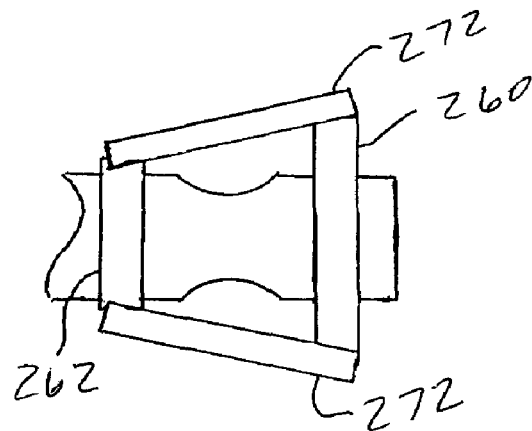
FIG. 27 shows a partial plan view of the expandable member of FIG. 26 with the node farthest away from the entry point of the expandable member into a tissue space expanded to loosen tissue to form a conical cavity that is enlarged away from the point of entry of the expandable member into a tissue space.
Figure 28:
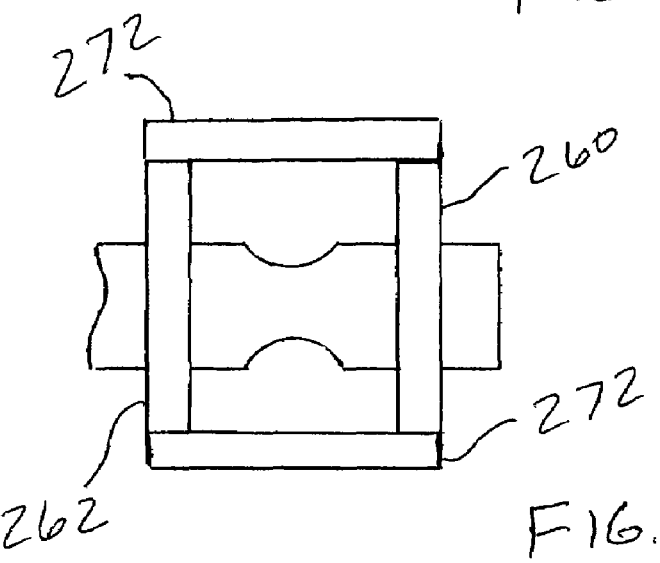
FIG. 28 shows a partial plan view of the expandable member of FIG. 26 with both nodes expanded to loosen tissue to form a cylindrical cavity.
Figure 29:
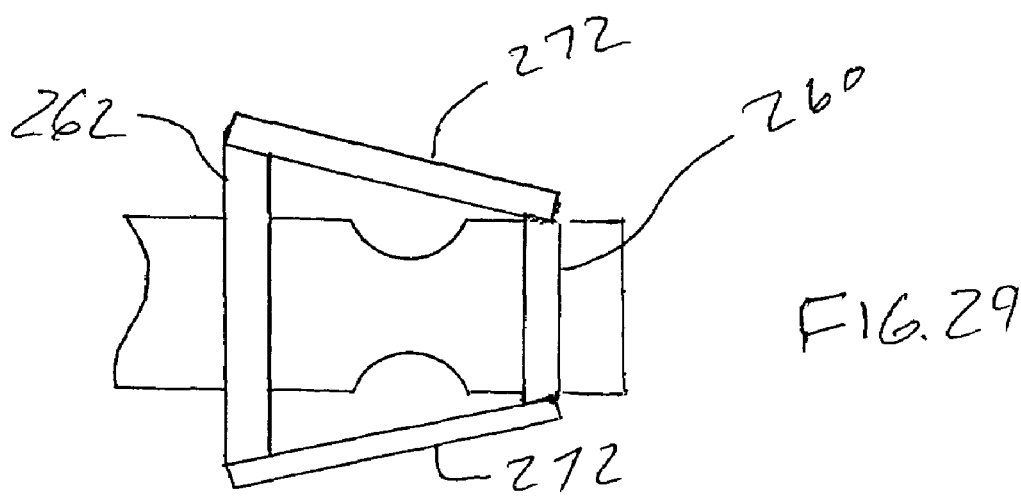
FIG. 29 shows a partial plan view of the expandable member of FIG. 26 with the node nearest the entry point of the expandable member into a tissue space expanded to loosen tissue to form a conical cavity that is enlarged closer to the point of entry of the expandable member into a tissue space.

Operation of the intervertebral tissue removal system 250 is substantially the same as operation of the intervertebral tissue removal system 200. The main difference is the shape of a cavity formed by selective filling of the nodes 260 and 262. Filling only node 260 provides the configuration shown in FIG. 27 which may be used to form a conical cavity which is enlarged in the direction away from the entry point of the node 260 into the tissue. The additional inflation of the node 262 results in the configuration shown in FIG. 28 which may be used to form a cylindrical cavity. Finally, filling only the node 262 provides the configuration shown in FIG. 29 which may be used to form a conical cavity which is oriented opposite to the conical cavity of FIG. 27.

Figure 30:
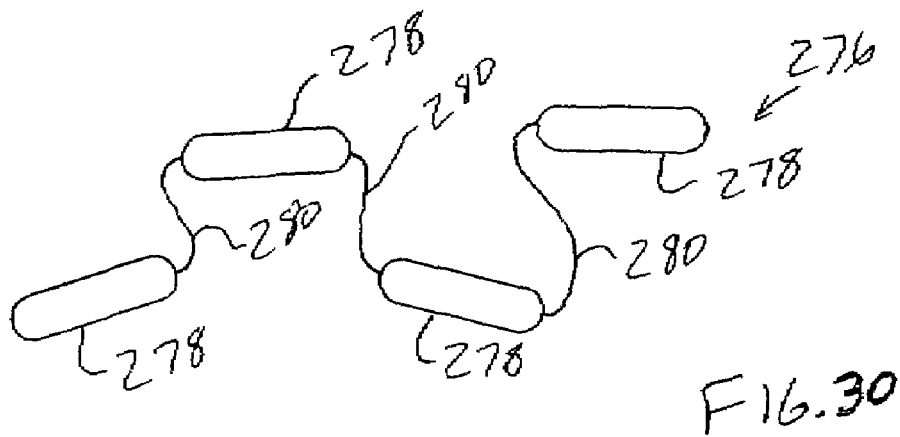
FIG. 30 shows an expansion media in the form of elongated segments that are inter connected incorporating principles of the present invention.
Figure 31:
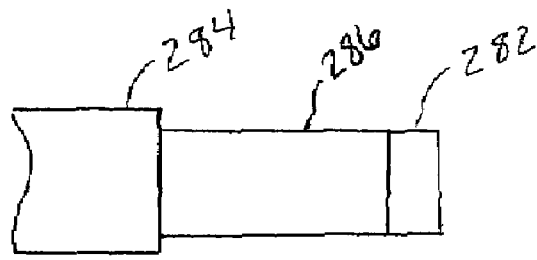
FIG. 31 shows a partial schematic view of an intervertebral tissue removal system which can be used with the segmented expansion media of FIG. 30 incorporating principles of the present invention.
Figure 32:
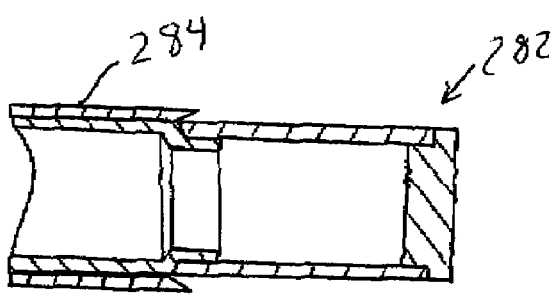
FIG. 32 shows a partial cross-sectional view of the system of FIG. 31.

In an alternative embodiment, segmented expansion media 276 shown in FIG. 30 is used to expand an expandable member. The segmented expansion media 276 includes a number of elongated segments 278 which are linked by connectors 280. Alternatively, the segments may be interconnected by a single connector which extends through each of the segments with the segments allowed to slide along the connector.

Figure 33:
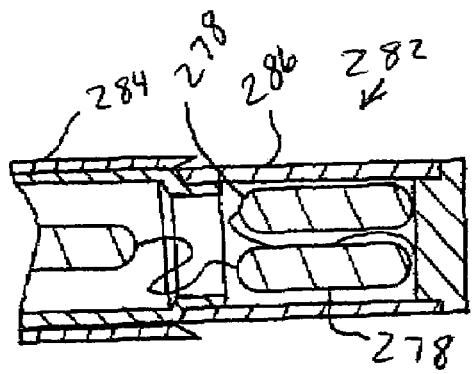
FIG. 33 is a partial cross-sectional view of the system of FIG. 31 with segmented expansion media within the expandable member prior to deformation of the expandable member.
Figure 34:
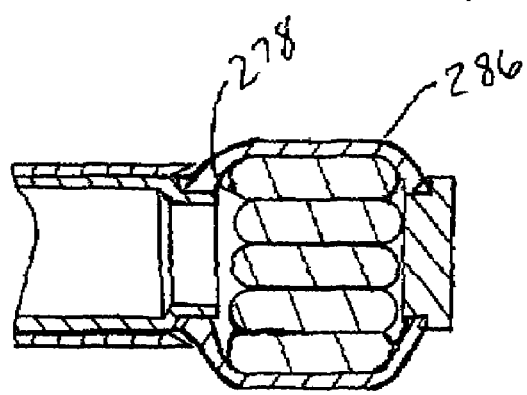
FIG. 34 a partial cross-sectional view of the system of FIG. 31 with segmented expansion media expanding the node of the expandable member.

Operation of a system incorporating the elongated segmented expansion media 276 is explained with reference to FIGS. 31-36. Expandable member 282 is sized to be inserted through a cannula 284 and includes a node 286. An abrading member (not shown) may be adhered to the node 286. Initially, the expandable member 282 is inserted through the cannula 284 in a deflated condition. A tool (not shown) is then used to insert the elongated segments 278 into the expandable member 282 until the node 286 is full as shown in FIG. 33. The node 286 is formed from a deformable material. Thus, continued insertion of the segmented expansion media 276 into the node 286 as shown in FIG. 34 causes the node 286 to be expanded to an enlarged condition.

Figure 35:
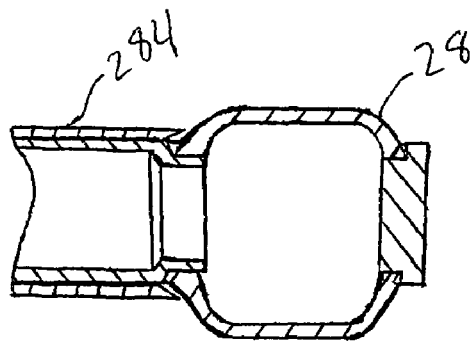
FIG. 35 shows a cross-sectional view of the system of FIG. 31 after the non-resilient node has been deformed with segmented media and after the segmented media has been withdrawn.
Figure 36:
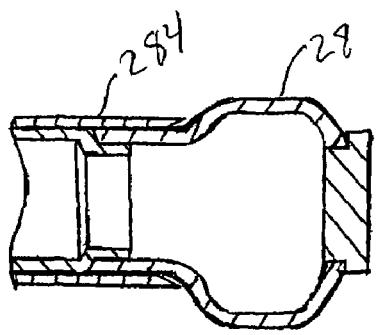
FIG. 36 shows a cross-sectional view of the system of FIG. 35 with the deformed node partially compressed as the expandable member is pulled into the cannula.

After the expandable member 282 has been manipulated to form a cavity, the segmented expansion media 276 is removed. The material used to form the node 286 in this embodiment is not resilient. Thus, as shown in FIG. 35, the node 286 remains in an expanded condition after the segmented expansion media 276 has been removed. Without the internal support provided by the segmented expansion media 276, however, the node 286 may be collapsed by forcing the node 286 against the lip of the cannula 284 as shown in FIG. 36.

Figure 37:
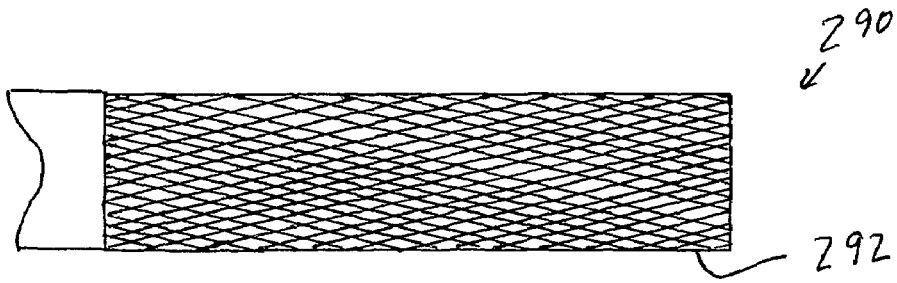
FIG. 37 shows a partial plan view of an alternative expandable member with a node that includes a number of strands wherein the strands provide the abrading members in accordance with principles of the present invention.
Figure 38:
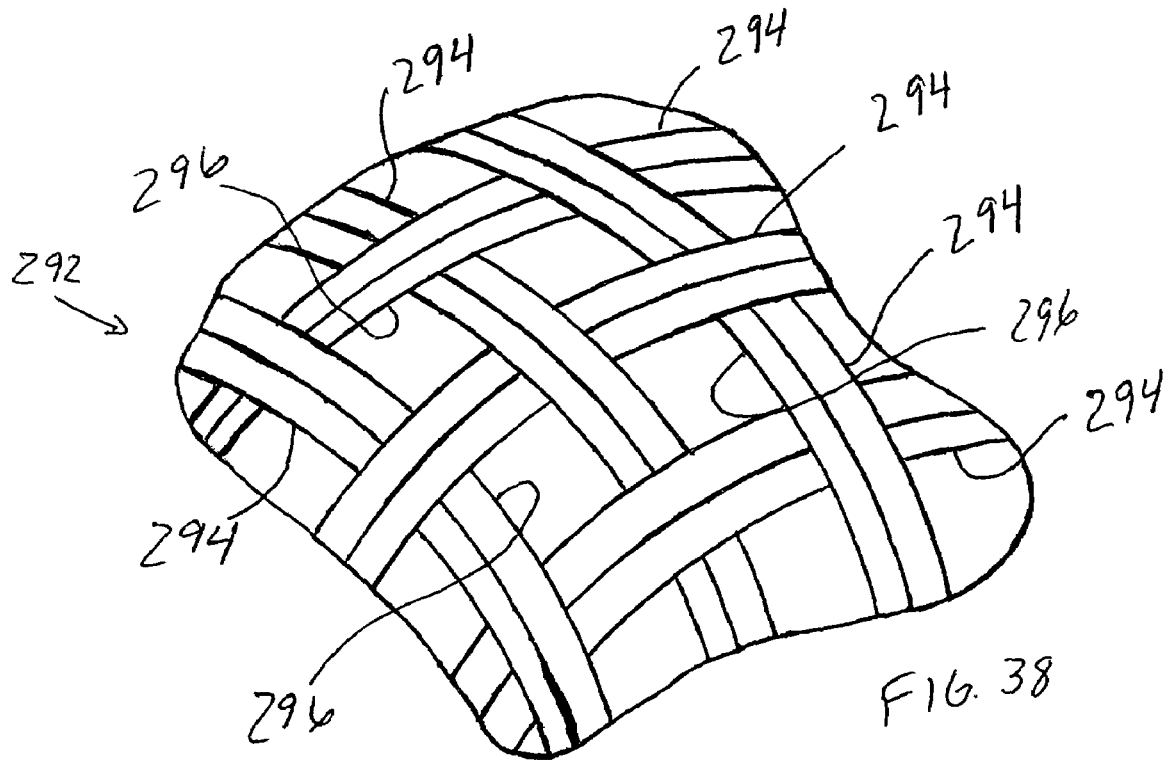
FIG. 38 shows a partial perspective view of the node of the expandable member of FIG. 37 in a fully expanded condition with openings between the strands.
Figure 39:
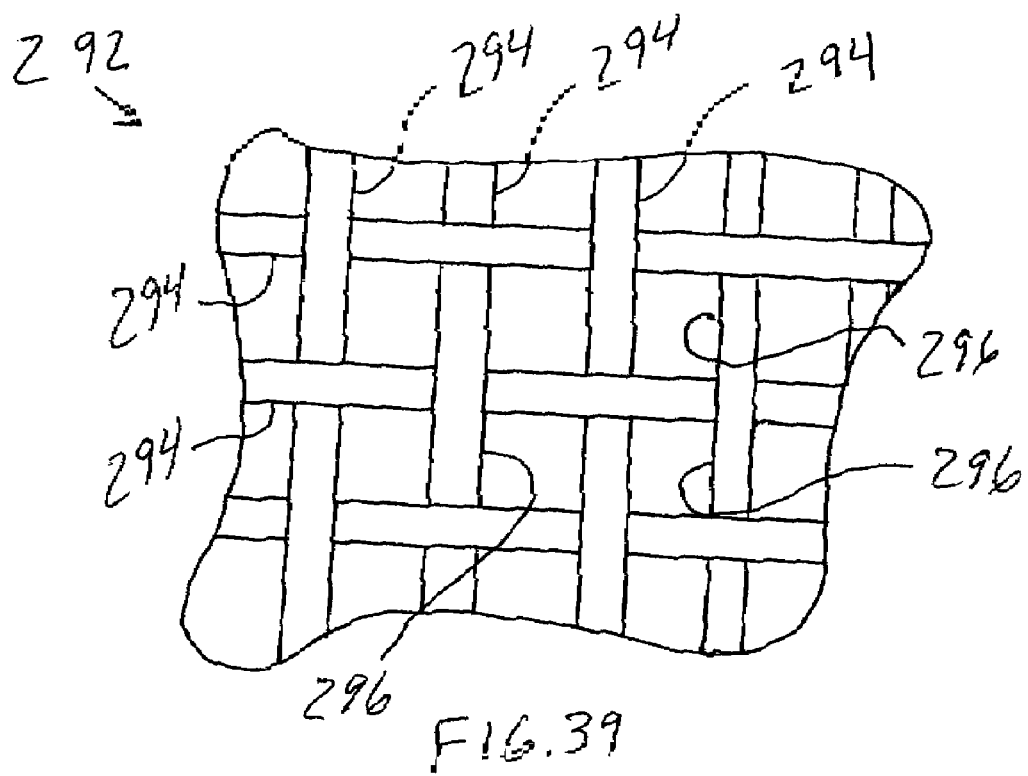
FIG. 39 shows a partial plan view of the node of the expandable member of FIG. 37 in a fully expanded condition with openings between the strands.

FIG. 37 shows an alternative expandable member 290 that includes a node 292 including a plurality of strands 294. With reference to FIGS. 38 and 39, which show an expanded portion of the expandable member 290, the node 292 is formed in a net-like pattern. Thus, the strands 294 define a number of openings 296. The openings 296 may be formed in a number of ways. For example, portions of a metal plate may be removed, leaving a pattern of openings defined by the remaining metal. Alternatively, individual wires may be woven into a basket and some or all of the wire junctions may be soldered. Moreover, the openings may be configured to form shapes other than rectangular shapes. The salient characteristic in this embodiment is that the openings 296, even when the node 292 is fully expanded, must be smaller than at least some of the media used to expand the expandable member 290.

Figure 40:
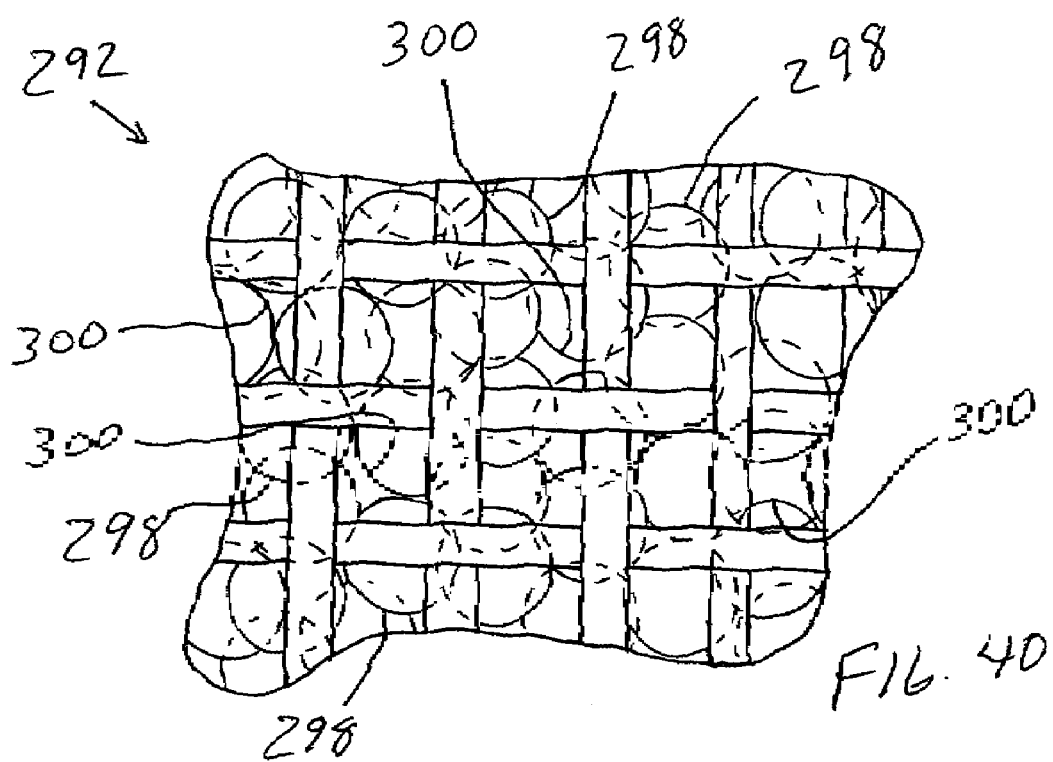
FIG. 40 shows a partial plan view of the node of the expandable member of FIG. 37 expanded by a generally spherical expansion media which is sized to not fit through the openings between the strands.

By way of example, FIG. 40 depicts a portion of the node 292 which has been expanded using a segmented expansion media 298. The segmented expansion media 298 is generally spherical. The diameter of the individual segments of the segmented expansion media 298 is selected such that the segmented expansion media 298 cannot pass through the openings 296. Thus, as the segmented expansion media 298 is forced into the expandable member 290, the node 292 is forced into an expanded condition. In this embodiment, the segmented expansion media 298 is not inter-connected.

The use of segmented expansion media further allows for the passage of fluid through the same conduit used to introduce the segmented media. As shown most clearly in FIG. 40, even when the segmented expansion media 298 is tightly packed, interstitial spaces 300 provide a pathway for fluid through the segmented expansion media 298. When the interstitial spaces 300 are significantly larger than the loosened pieces of tissue formed by abrading a cavity, the interstitial spaces 300 may be used to drain aspiration fluid and loosened tissue. In one such embodiment, the curvature of the segmented media is selected such that the segmented media cannot extend outside of the cutting envelope defined by the outer surface of the strands 294.

As the pieces of loosened tissue approach the size of the interstitial spaces 300, however, the segmented expansion media 298 may function as a filter. Thus, as tissue is abraded, the interstitial spaces 300 may clog with the loosened tissue. When the interstitial spaces 300 clog with the loosened tissue, the expandable member 290 may be removed and the interstitial spaces 300 flushed to remove the loosened tissue. Alternatively, the interstitial spaces 300 may be used as conduits to provide aspirating fluid to the tissue cavity, with drainage of the aspiration fluid and loosened tissue provided through a separate conduit.

In the embodiment of FIG. 38, the strands 294 of the node 292 have a generally rectangular cross-section. Thus, the corners of the strands 94 function as abrading members that loosen tissue as the expandable member 290 is manipulated within, for example, a disc. In alternative embodiments, the strands may be other shapes such as circular or triangular (e.g. wedge wire). Additionally, the orientation of the strands may be modified to present different cutting angles to the tissue to be loosened as the expandable member is manipulated to clear a cavity.

Figure 41:
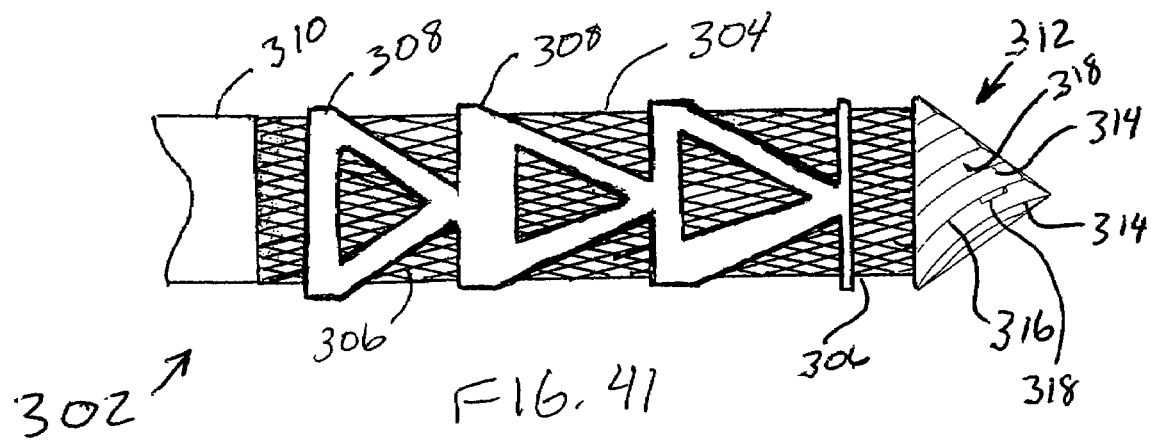
FIG. 41 shows a plan view of an alternative expandable member with a node that includes a number of strands and support ribbing to divide the node into a plurality of shaped nodes which can be used without a cannula in accordance with principles of the present invention.
Figure 42:
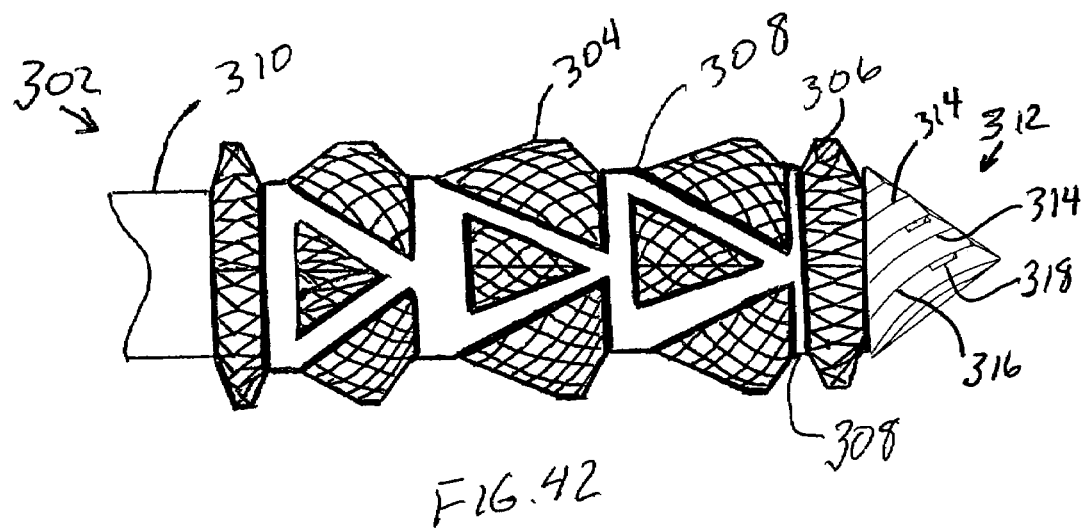
FIG. 42 shows a plan view of the expandable member of FIG. 41 in an expanded condition.

Additionally, the node may be configured to provide different shapes. For example, the expandable tool 302 shown in FIG. 41 includes a node 304 with strands 306. Ribbing 308 is provided about the strands 306. The strands 306 are coupled to a conduit 310 at one end and to a tip 312 at the other end. The ribbing 308 is constructed of a material that is more rigid than the strands 306. Thus, when the node 304 is expanded, the ribbing 308 constrains the strands 306 resulting in the shape shown in FIG. 42. The ribbing 308 thus functions to divide the node 304 into a plurality of nodes of different shapes. In this embodiment, the strands 306 are not fixedly attached to the ribbing 308. In alternative embodiments, the strands may be coupled to the ribbing. In further alternative embodiments, the ribbing is provided integrally with the conduit and the node is attached to the outer surface of the ribbing.

The tip 312 in this embodiment is further configured to provide access to an area in which tissue is to be loosened. The tip 312 includes a plurality of cutting edges 314 which define flutes 316. The cutting edges 314 loosen tissue when the expandable tool 302 is rotated so as to allow the forward movement of the expandable tool 302 into the area in which tissue is to be removed. The tip 312 further includes aspiration supply orifices 318. The aspiration supply orifices 318 provide aspiration fluid from an aspiration fluid supply conduit (not shown) within the conduit 310. The aspiration fluid and loosened tissue may then removed through the openings between the strands 306 and the interstitial spaces between the expansion media in a manner similar to that discussed above with respect to FIG. 40.

In an alternative embodiment shown in FIG. 43, an intervertebral tissue removal system 320 includes a cannula 322, a conduit 324 and an expandable member 326. The expandable member 326 includes a node 328 which is operably coupled to an abrading member 330. A guide rod 332 is located within the inner bore 334 of the conduit 324 and an orifice 336 extends from the inner bore 334 to the outer surface of the conduit 324. The intervertebral tissue removal system 320 also includes a collection tube 336.

The conduit 324 in this embodiment is made of a flexible material. Accordingly, the conduit 324 may be bent or twisted. The conduit 324 is not, however, radially flexible. Thus, as pressure in the inner bore 334 increased, the volume of the inner bore 334 does not increase appreciably. Accordingly, the guide rod 332 provides the structural rigidity for the conduit 324.

The guide rod 332 in this embodiment is constructed of an inherent memory metal such as nitinol, commercially available from Memry Corporation of Bethel, Conn. Inherent memory metals are imbued with a "memory" such that the particular shape of a device made from the metal can be "programmed" into the metal so that when a particular external condition is present, the device alters its shape to the programmed shape. The external condition may be thermal or electrical, such as a magnetic field. In this embodiment, the guide rod 332 is configured to maintain a substantially straight configuration at room temperature. When exposed to a higher temperature, however, the guide rod 332 changes to the shape shown in FIG. 44.

The intervertebral tissue removal system 320 is operated much in the same manner as the intervertebral tissue removal system 100 of FIG. 1. The main difference is that in the embodiment of FIGS. 43 and 44, the saline solution which is used to expand the node 328 is provided at a temperature which also causes the guide rod 332 to curve into the shape shown in FIG. 44. Of course, by modifying the temperature of the saline solution, a greater or lesser amount of curvature may be achieved.

Alternatively, the guide rod 332 may be configured to change shape when exposed to body temperature. In further alternative embodiments, the shape of the guide rod may be controlled by a magnetic field or the guide rod may be formed as a bimetallic rod comprising metals with different thermal expansion characteristics. In yet another embodiment, a guide rod may be made from a flexible, shape retaining material which formed to present an angled shape in a relaxed condition. In this embodiment, the guide rod is deformed for insertion within a cannula. As the guide rod exits the cannula, the guide rod attempts to return to the angled shape, thereby providing pressure against tissue, allowing an abrasive member to then loosen the tissue. In any event, once the abrasive member 330 is in the desired position as a function of both the expansion of the node 328 as well as the shape of the guide rod 332, tissue may be loosened to create the desired cavity.

Depending upon the particular configuration, intervertebral tissue removal system components may be made from a variety of materials in addition to the materials identified above. For example, the abrading member may be constructed from stainless steel, titanium, polymers, polyesters, or polyurethanes. The expansion device may be made from rigid or compliant materials including stainless steel, titanium, memory metals, silicones, polyesters, polyurethanes, poly ether ether ketone (PEEK) or polypropylenes. Additionally, the materials may be used to deliver chemicals to the area in which a cavity is to be formed. By way of example, but not of limitation, any of the various components may be imbedded or coated with a medication for relieving pain or with an enzyme for dissolving tissue.

While the present invention has been illustrated by the description of exemplary processes and system components, and while the various processes and components have been described in considerable detail, applicant does not intend to restrict or in any way limit the scope of the appended claims to such detail. Additional advantages and modifications will also readily appear to those ordinarily skilled in the art. The invention in its broadest aspects is therefore not limited to the specific details, implementations, or illustrative examples shown and described. Accordingly, departures may be made from such details without departing from the spirit or scope of applicant's general inventive concept.

We claim:

1. An intervertebral tissue removal system comprising:
   at least one abrading member for abrading tissue in an area to be cleared;
   at least one expandable member including a housing and at least one node, the node operable to be expanded from a first condition to a second condition, wherein a first end portion of the at least one abrading member is fixed to the housing and the volume defined by the at least one expandable member in the second condition is greater than the volume defined by the at least one expandable member in the first condition, the at least one expandable member operably connected to a second portion of the at least one abrading member that is not fixed to the housing such that as the at least one node expands from the first condition to the second condition, the at least one abrading member is pivoted by the at least one node from a first position to a second position;
   an expansion media for insertion within the at least one expandable member; and
   an expansion media conduit connected to the at least one expandable member for delivering the expansion media to the at least one expandable member to expand the at least one expandable member from the first condition to the second condition.

2. The intervertebral tissue removal system of claim 1, wherein the expansion media comprises a fluid, the system further comprising:
   a fluid supply system fluidly connected to the at least one node through the expansion media conduit for delivering the fluid from a fluid reservoir to the at least one expandable node at a pressure sufficient to expand the at least one node from the first condition to the second condition.

3. The intervertebral tissue removal system of claim 2, wherein the at least one node is configured to expand symmetrically about a longitudinal axis of the at least one node as the at least one node is expanded from the first condition to the second condition.

4. The intervertebral tissue removal system of claim 2, wherein the at least one node is configured to expand symmetrically along a longitudinal axis of the at least one node as the at least one node is expanded from the first condition to the second condition.

5. The intervertebral tissue removal system of claim 2, wherein the at least one abrading member comprises:
   a first abrading member configured to pivot about a first pivot axis: and
   a second abrading member configured to pivot about a second pivot axis, wherein the second pivot axis is longitudinally displaced from the first pivot axis along a longitudinal axis of the at least one expandable member.

6. The intervertebral tissue removal system of claim 2, wherein the at least one node comprises a plurality of nodes and the at least one abrading member comprises a plurality of abrading members, each of the plurality of abrading members associated with a respective one of the plurality of nodes.

7. The intervertebral tissue removal system of claim 6, further comprising:
an inter-nodal conduit fluidly connecting a first node and a second node of the plurality of nodes;
an aspiration conduit for removing abraded tissue from the area; and
an aspiration orifice fluidly connected to the aspiration conduit, the aspiration orifice located between the first and the second node.

8. The intervertebral tissue removal system of claim 7, wherein the expansion media conduit extends at least partially within the aspiration conduit.

9. The intervertebral tissue removal system of claim 2, wherein the fluid reservoir is a liquid reservoir.

10. The intervertebral tissue removal system of claim 9, further comprising:
an aspiration fluid outlet fluidly connected to the expanding fluid conduit such that the fluid reservoir provides aspiration fluid to the area to be cleared through the aspiration fluid outlet.

11. The intervertebral tissue removal system of claim 1, wherein the at least one abrading member comprises a chisel.

12. The intervertebral tissue removal system of claim 1, wherein the at least one abrading member comprises a blade.

13. The intervertebral tissue removal system of claim 1, wherein the at least one abrading member defines a flute extending along the at least one expandable member.

14. The intervertebral tissue removal system of claim 1, wherein the at least one abrading member comprises a plurality of abrasive particles.

15. The intervertebral tissue removal system of claim 1, wherein the at least one abrading member comprises a mesh.

16. The intervertebral tissue removal system of claim 1, further comprising:
a guide rod operably engaged to the at least one expandable member for guiding the at least one expandable member to a desired location within the area.

17. The intervertebral tissue removal system of claim 16, wherein the guide rod is controllably deformable between a first shape and a second shape.

18. The intervertebral tissue removal system of claim 17, wherein the guide rod comprises:
a first component having a first thermal coefficient of expansion; and
a second component having a second thermal coefficient of expansion, the second thermal coefficient of expansion larger than the first thermal coefficient of expansion, such that as the thermal environment of the guide rod changes, the first component and the second component undergo different expansion, thereby controllably deforming the guide rod.

19. The intervertebral tissue removal system of claim 17, wherein the guide rod comprises an inherent memory material.

20. The intervertebral tissue removal system of claim 19, wherein the inherent memory material is responsive to temperature.

21. The intervertebral tissue removal system of claim 20, further comprising:
a variable temperature fluid reservoir; and
an aspiration fluid outlet proximate to at least a portion of the guide rod and fluidly connected to the variable temperature fluid reservoir such that the fluid reservoir provides variable temperature fluid through the aspiration fluid outlet.

22. The intervertebral tissue removal system of claim 16, wherein the guide rod comprises a flexible shape retaining material.

23. The intervertebral tissue removal system of claim 1, further comprising:
a cannula for providing access to the area to be cleared, the cannula sized to receive the at least one expandable member when the at least one expandable member is in the first condition.

24. The intervertebral tissue removal system of claim 1, further comprising:
an aspiration fluid supply conduit within the expansion media conduit for providing aspiration fluid to the area to be cleared.

25. An intervertebral tissue removal system comprising:
at least one abrading member for abrading tissue in an area to be cleared;
at least one deformable member configured to be reversibly deformed from a first shape to a second shape, the at least one deformable member operably connected to the at least one abrading member such that as the at least one deformable member deforms from the first shape to the second shape, the at least one abrading member is moved from a first position to a second position;
a non-liquid segmented expansion media configured to be inserted within the at least one deformable member and configured to be removed from the at least one deformable member; and
an expansion media conduit connected to the at least one deformable member for delivering the expansion media to the at least one deformable member to deform the at least one deformable member from the first shape to the second shape.

26. The intervertebral tissue removal system of claim 25 wherein the at least one deformable member is configured to deform asymmetrically about a longitudinal axis of the at least one deformable member as the at least one deformable member is deformed from the first shape to the second shape.

27. The intervertebral tissue removal system of claim 25 wherein the at least one deformable member is configured to deform asymmetrically along a longitudinal axis of the at least one deformable member as the at least one deformable member is deformed from the first shape to the second shape.

28. The intervertebral tissue removal system of claim 25 wherein the at least one abrading member is configured to rotate from the first position to the second position as the least one expandable member is deformed from the first shape to the second shape.

29. The intervertebral tissue removal system of claim 25, wherein the at least one deformable member comprises a plurality of strands.

30. The intervertebral tissue removal system of claim 29, wherein the at least one abrading member comprises a portion of each of the plurality of strands.

31. The intervertebral tissue removal system of claim 29, wherein the at least one deformable member further comprises a rib for restricting the deformation of the plurality of strands.

32. The intervertebral tissue removal system of claim 25, wherein:
the at least one deformable member comprises a deformable mesh defining a plurality of holes therethrough, the holes sized such that when the mesh is deformed, the segmented media does not pass through the plurality of holes.

33. The intervertebral tissue removal system of claim 32, wherein the segmented media comprises a plurality of spherical segments.

34. The intervertebral tissue removal system of claim 25, wherein the segmented media comprises a plurality of elongated segments.

35. The intervertebral tissue removal system of claim 34, wherein the segmented media comprises a connector connecting at least a first and a second of the plurality of elongated segments.

36. The intervertebral tissue removal system of claim 25, wherein the at least one deformable member comprises a resilient material such that the at least one deformable member returns to the first shape from the second shape when the expansion media is removed from the at least one deformable member.

37. The intervertebral tissue removal system of claim 25, further comprising:
a cannula for providing access to the area to be cleared, the cannula sized to receive the at least one deformable member when the at least one deformable member is in the first shape.

38. A method of loosening intervertebral tissue comprising:
inserting at least one abrading member for abrading tissue into an area to be cleared;
expanding at least one expandable member from a first condition to a second condition, wherein the volume defined by the at least one expandable member in the second condition is greater than the volume defined by the at least one expandable member in the first condition;
moving a portion of the inserted at least one abrading member that is not affixed to a housing of the at least one expandable member from a first position to a second position by the expansion of the at least one expandable member while a second portion of the at least one abrading member is fixed to a housing of the at least one expandable member;
manipulating the inserted at least one abrading member to loosen tissue; and
removing the loosened tissue from the area to be cleared.

39. The method of claim 38, wherein:
inserting comprises inserting the at least one abrading member through a cannula into the area; and
expanding comprises delivering a fluid from a fluid reservoir to the at least one expandable member at a pressure sufficient to expand the at least one expandable member from the first condition to the second condition.

40. The method of claim 39, further comprising:
aspirating the area with the fluid.

41. The method of claim 38, further comprising:
providing aspiration fluid to the area through a conduit located within a conduit used to provide expansion media to the at least one expandable member.

42. The method of claim 38, wherein moving the inserted at least one abrading member comprises rotating the at least one abrading member from the first position to the second position.

43. The method of claim 38, further comprising, after manipulating the inserted at least one abrading member:
expanding the inserted at least one expandable member from the second condition to a third condition, wherein the volume defined by the at least one expandable member in the third condition is greater than the volume defined by the at least one expandable member in the second condition;
moving the inserted at least one abrading member from the second position to a third position by the expansion of the at least one expandable member to the third condition;
manipulating the at least one abrading member in the third position to loosen additional tissue; and
removing the additionally loosened tissue from the area to be cleared.

44. The method of claim 38, further comprising:
reducing the at least one expandable member from the second condition to a fourth condition, wherein the volume defined by the at least one expandable member in the second condition is greater than the volume defined by the at least one expandable member in the fourth condition;
moving at least one abrading member from the second position to a fourth position by the reduction of the at least one expandable member; and
removing the reduced at least one expandable member from the area.

45. The method of claim 38, further comprising:
guiding the inserted at least one expandable member to a desired location within the area with a guide rod.

46. The method of claim 45, wherein guiding comprises:
controllably deforming the guide rod between a first shape and a second shape.

47. The method of claim 45, wherein the guide rod is controllably deformed prior to insertion within a cannula.

48. The method of claim 45, wherein the guide rod is controllably deformed after passing through a cannula.

49. The method of claim 38, wherein expanding comprises:
inserting a segmented media into the at least one expandable member.

* * * * *